United States Patent
Carson et al.

(10) Patent No.: US 8,101,760 B2
(45) Date of Patent: *Jan. 24, 2012

(54) GLUCOCORTICOID RECEPTOR MODULATOR AND METHODS OF USE

(75) Inventors: Matthew William Carson, Fishers, IN (US); Michael Joseph Coghlan, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/305,295

(22) PCT Filed: Jul. 12, 2007

(86) PCT No.: PCT/US2007/073345
§ 371 (c)(1),
(2), (4) Date: Dec. 17, 2008

(87) PCT Pub. No.: WO2008/008882
PCT Pub. Date: Jan. 17, 2008

(65) Prior Publication Data
US 2010/0069425 A1    Mar. 18, 2010

(51) Int. Cl.
*C07D 455/03* (2006.01)
*C07D 313/10* (2006.01)
*A61K 31/4353* (2006.01)

(52) U.S. Cl. ............... 546/80; 546/89; 546/93; 514/291

(58) Field of Classification Search ............ 546/80, 546/89, 93; 514/291
See application file for complete search history.

(56) References Cited

U.S. PATENT DOCUMENTS

| | | |
|---|---|---|
| 4,999,363 A | 3/1991 | Oshima et al. |
| 5,024,912 A | 6/1991 | Neishi et al. |
| 5,093,210 A | 3/1992 | Ohta et al. |
| 5,378,701 A | 1/1995 | Ohshima et al. |

FOREIGN PATENT DOCUMENTS

| | | |
|---|---|---|
| JP | 01161245 | 6/1989 |
| WO | WO 99/33786 | 7/1999 |
| WO | WO 00/59884 | 10/2000 |
| WO | WO 2004/043965 | 5/2004 |
| WO | WO 2004/052847 | 6/2004 |

OTHER PUBLICATIONS

Carson, "New Vistas in the Search for a Selective Glucocorticoid Receptor Modulator (SGRM)," oral presentation at Cambridge Health Institute, Cambridge, MA, Oct. 18, 2007.
Coghlan, "Nuclear Hormone Receptor Research," oral presentation at 28th Gulf Coast Chemistry Conference, Pensacola, FL, Aug. 24, 2006.
Jadhav, "Discovery of orally bioavailable, nonsteroidal mineralocorticoid receptor antagonists: A tale of three platforms," oral presentation at ACS National Meeting, Atlanta, GA., Mar. 25-30, 2006.
Jadhav, "Discovery of First, Orally Bioavailable, Nonsteroidal Mineralocorticoid Receptor Antagonist," oral presentation at Gordon Research Conference, Newport, RI, Jul. 4-9, 2004.
Yu, et al., "Cyclocarbopalladation of Alkynes: A Stereoselective Method for Preparing Dibenzoxapine Containing Tetrasubstituted Exocyclic Alkenes," Organic Letters, vol. 8, No. 8, pp. 1685-1688 (2006).
Yu, "Stereoselective Synthesis of Dibenzoxapine Containing Nuclear Hormone Receptor Modulators through Palladium-Catalyzed Cascade Reactions," oral presentation at Gordon Research Conference, Smithfield, RI, Jul. 16-21, 2006.

*Primary Examiner* — Rita Desai
(74) *Attorney, Agent, or Firm* — Elizabeth Dingess-Hammond; Alexander Wilson

(57) ABSTRACT

The present invention provides Compound (I): Compound (I) or a pharmaceutically acceptable salt thereof; pharmaceutical compositions comprising Compound (I) in combination with one or more pharmaceutically acceptable carriers, excipients, or diluents; and methods for the treatment of inflammatory and immune disorders comprising administering to a patient in need thereof an effective amount of Compound (I) or a pharmaceutically acceptable salt thereof.

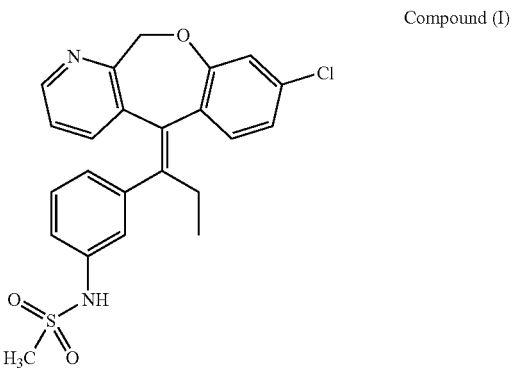

Compound (I)

7 Claims, No Drawings

GLUCOCORTICOID RECEPTOR MODULATOR AND METHODS OF USE

TECHNICAL FIELD OF INVENTION

The present invention relates to tricyclic compounds that are useful as therapeutic agents in the treatment of inflammatory and immune disorders responsive to steroidal glucocorticoids, to pharmaceutical compositions comprising the compounds, to methods of using the compounds to treat inflammatory and immune disorders in patients, and to intermediates and processes useful in the synthesis of the compounds.

BACKGROUND OF INVENTION

Naturally occurring as well as synthetic steroidal glucocorticoids (e.g. cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis. Thus, there remains a need for alternative therapies which possess the beneficial effects of steroidal glucocorticoids, but with a reduced likelihood or incidence of attendant side effects.

Glucocorticoids exert their pharmacological effects by regulating gene transcription after the formation of a complex with the glucocorticoid receptor (GR). This GR-glucocorticoid complex affects gene transcription by distinct mechanisms. First, following binding of the glucocorticoid, the complexed GR translocates to the nucleus where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

The search for GR ligands suitable as replacements for steroidal glucocorticoids is hindered by the fact that the other steroid hormone receptors, for example the androgen receptor (AR), the mineralocorticoid receptor (MR), and the progesterone receptor (PR), which mediate other physiological processes, have ligand binding domains homologous to GR. As a result, GR ligands have a potential for cross reactivity with these other receptors. Thus, a desired attribute of a replacement for steroidal glucocorticoids is that it binds to GR with greater affinity relative to the other steroid hormone receptors.

Recent insights have provided an opportunity for the identification of GR ligands with potent anti-inflammatory properties relative to their propensity for inducing side effects associated with glucocorticoid therapy. Glucocorticoids have long been known to repress the endogenous production of pro-inflammatory proteins such as interleukin-6 (IL-6) and tumor necrosis factor-alpha (TNFα).

Significantly, it has been reported that ligands selectively acting via the DNA-binding independent function of GR should suffice for the treatment of inflammatory diseases. Reichardt et al., *EMBO J.*, 20: 7168-7173 (2001). Furthermore, many side effects of glucocorticoid therapy (e.g. hyperglycemia, diabetes mellitus, glaucoma, and muscle atrophy) are reported to be mediated by transactivational mechanisms following GR binding to DNA (see Shacke et al., *Pharmacol. & Therap.*, 96(1): 23-43 (2002)). Thus, an agent which is capable of differentiating GR-mediated transrepression from GR-mediated transactivation is particularly desirable. Furthermore, an agent that displays limited capacity to modulate (i.e. agonize, partially agonize, partially antagonize, or antagonize) the transcriptional activity of the other steroid hormone receptors is also particularly desirable.

Thus, it is an object of the present invention to provide an agent which binds to GR with greater affinity relative to the other steroid hormone receptors. More particularly it is an object to provide an agent which binds to GR with 30-fold greater affinity relative to AR, MR, and PR. It is a further object of the present invention to provide an agent which possesses potent anti-inflammatory properties relative to its propensity for inducing side effects associated with glucocorticoid therapy. More particularly, it is an object to provide an agent which possesses potent anti-inflammatory properties relative to its propensity for inducing bone loss or osteoporosis. It is a further object of the present invention to provide an agent which displays limited capacity to modulate the activity of other steroid hormone receptors.

Tricyclic GR modulators are known in the art. For example WO 04/052847 discloses a genus of tricyclic steroid hormone receptor modulators which are useful for treating disorders susceptible to mineralocorticoid receptor or glucocorticoid receptor modulation. WO 99/33786 discloses triphenylpropanamide-derivative compounds that bind the glucocorticoid receptor and have anti-inflammatory properties.

SUMMARY OF THE INVENTION

It has now been found that by selecting a compound from within the scope of WO 04/052847, which is provided as Compound (I) herein below, a novel therapeutic agent has been identified which possesses a particular profile of activity that suggests it is particularly useful in the treatment of inflammatory and immune disorders responsive to steroidal glucocorticoids. Accordingly, the present invention provides Compound (I):

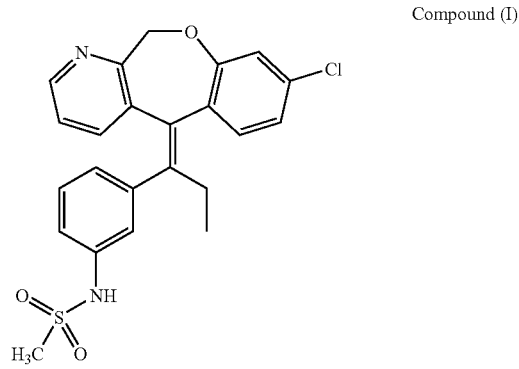

Compound (I)

((E)-N-{3-[1-(8-Chloro-11H-10-oxa-1-aza-dibenzo[a,d]cyclohepten-5-ylidene)-propyl]-phenyl}-methanesulfonamide)

or a pharmaceutically acceptable salt thereof.

As a particular embodiment, the present invention provides Compound (I) in crystalline form.

In another embodiment, the present invention provides a method of treating an inflammatory or immune disorder, particularly rheumatoid arthritis, comprising administering to a patient in need thereof an effective amount of Compound (I), or a pharmaceutically acceptable salt thereof.

In another embodiment, the present invention provides the use of Compound (I), or a pharmaceutically acceptable salt thereof, for the manufacture of a medicament for treating an inflammatory or immune disorder, particularly rheumatoid arthritis. In addition, the present invention provides Compound (I), or a pharmaceutically acceptable salt thereof, for use in therapy.

In another embodiment, the present invention provides a pharmaceutical composition comprising Compound (I), or a pharmaceutically acceptable salt thereof, in combination with one or more pharmaceutically acceptable carriers, excipients, or diluents. As a preferred embodiment, the present invention provides a pharmaceutical composition for the treatment of rheumatoid arthritis comprising Compound (I), or a pharmaceutically acceptable salt thereof, in combination one or more pharmaceutically acceptable carriers, excipients, or diluents. In addition, the present invention also provides novel intermediates and processes for the synthesis of Compound (I).

DETAILED DESCRIPTION OF THE INVENTION

The present invention provides Compound (I) which possesses a profile of activity which makes it particularly useful in the treatment of inflammatory and immune disorders responsive to steroidal glucocorticoids. As evidenced by in vitro and in vivo testing, Compound (I) binds to GR with greater affinity relative to other steroid hormone receptors and displays potent anti-inflammatory properties relative to its propensity for inducing side effects associated with glucocorticoid therapy. In addition, Compound (I) displays only a limited capacity to modulate the activity of the other steroid hormone receptors AR, MR, and PR. Further still, Compound (I) possesses yet additional technical effects or advantageous properties, as further discussed herein, which address other problems in the field of patient therapy and pharmaceutical development.

The present invention also provides the use of Compound (I) for the treatment of inflammatory and immune disorders responsive to steroidal glucocorticoids. Such disorders include, for example, rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. A particular disorder for which Compound (I) is useful is rheumatoid arthritis. Rheumatoid arthritis (RA) is a chronic disorder characterized by persistent joint synovial tissue inflammation with a typical age of onset between 30 and 50 years of age. RA is the most common form of inflammatory arthritis with a prevalence estimated to be about 0.8 percent of the world population, with women being twice as likely as men to develop the disease. Rindfleisch et al., *Am. Fam. Physician*, 72(6): 1037-1047 (2005).

The use of Compound (I) for the treatment of inflammatory and immune disorders is also believed to be associated with a reduced propensity, likelihood, or incidence of side effects typically associated with glucocorticoid therapy. One such side effect of glucocorticoid therapy is bone loss/osteoporosis or glucocorticoid induced osteoporosis (GIOP). GIOP is the most common cause of drug induced osteoporosis and has been reported to occur in up to fifty percent of patients undergoing chronic (i.e. lasting longer than six months) glucocorticoid therapy. Feldstein et al., *Osteoporos. Int.*, 16: 2168-2174 (2005). In particular, the use of Compound (I) is believed to be associated with a reduced propensity, likelihood, or incidence of bone loss or osteoporosis.

Unless otherwise defined, this invention includes pharmaceutically acceptable salts of Compound (I) as well as solvates of the free base of Compound (I) or a pharmaceutically acceptable salt thereof. The term "pharmaceutically acceptable salt" as used herein, refers to salts of Compound (I) which are substantially non-toxic to living organisms. Examples of pharmaceutically acceptable salts and methods for their preparation are conventional in the art. See for example, Stahl et al., "Handbook of Pharmaceutical Salts: Properties, Selection and Use", VCHA/Wiley-VCH, (2002); Gould, P. L., "Salt selection for basic drugs", *International Journal of Pharmaceutics*, 33: 201-217 (1986); and Bastin et al. "Salt Selection and Optimization Procedures for Pharmaceutical New Chemical Entities", *Organic Process Research and Development*, 4: 427-435 (2000). Particular mention is made of the hydrogen chloride salt, the hydrogen bromide salt, and the hemisulfate salt, however it is to be understood that the free base of Compound (I) is preferred.

As used herein the term "patient" refers to a human or nonhuman mammal such as a dog, cat, cow, monkey, horse, or sheep. More particularly, the term "patient" refers to a human. The term "treating" (or "treat" or "treatment") as used herein includes prohibiting, preventing, restraining, slowing, stopping, or reversing the progression or severity of a symptom or disorder.

Compound (I), or a pharmaceutically acceptable salt thereof, may be formulated for administration as part of a pharmaceutical composition. As such, pharmaceutical compositions comprising Compound (I), or a pharmaceutically acceptable salt thereof, in combination with one or more pharmaceutically acceptable carriers, excipients, or diluents are an important embodiment of the invention. Examples of pharmaceutical compositions and methods for their preparation are well known in the art. See, e.g. REMINGTON: THE SCIENCE AND PRACTICE OF PHARMACY, A. Gennaro, et al., eds., 19$^{th}$ ed., Mack Publishing (1995). Illustrative compositions comprising Compound (I) include, for example: Compound (I) in suspension with 1% sodium carboxymethyl cellulose, 0.25% polysorbate 80, and 0.05% Antifoam 1510™ (Dow Corning); Compound (I) in nanosuspension with 1% sodium carboxymethyl cellulose, 0.25% polysorbate 80, and 0.05% Antifoam 1510; and Compound (I) in suspension with 0.5% methylcellulose, 1% sodium lauryl sulfate, and 0.1% Antifoam 1510 in 0.01N HCl. Particular compositions comprising Compound (I) are provided below:

| Compound (I) formulated in Oral Solution | |
|---|---|
| Ingredient | Concentration |
| Compound (I) | 0.1 mg/ml |
| HP-β-CD | 10% (w/v) |
| Peppermint flavor | 0.03% (v/v) |
| Water irrigation | Up to 100% |

For example, 50.0 g hydroxypropyl-β-cyclodextrin (HP-β-CD) (Roquette) is added to a 500 mL beaker followed by approximately 400 mL of water for irrigation and the mixture is magnetically stirred for about 30 minutes to dissolve the HP-β-CD. 50.0 mg of Compound (I), particularly in micronized form, is added to the HP-β-CD solution and the mixture is covered with continued stirring (approximately 2 h) to dissolve the Compound. Peppermint flavor (0.15 mL) is added to the mixture with continued stirring to disperse the flavor. The solution is transferred to a volumetric flask and additional water for irrigation is added to bring the final volume to 500 mL.

Compound (I) formulated in Oral Suspension Vehicle

| SuspensionVehicle Ingredient | Concentration |
| --- | --- |
| Methocel E5-LV | 1.5% (w/v) |
| Sorbitol liquid | 10% (w/v) |
| Sodium saccharin | 0.08% (w/v) |
| Tween 80 | 0.25% (w/v) |
| Antifoam 1510 | 0.05% (v/v) |
| Peppermint flavor | 0.03% (v/v) |
| Water for irrigation | Up to 100% |

For example, 1.25 g of Tween 80 (Fluka) is added to a 500 mL beaker followed by 7.5 g of hydroxypropyl methylcellulose (Methocel E5-LV, Colorcon) and 0.4 g of sodium saccharin (Sigma). Approximately 300 mL of water for irrigation is added to the beaker and the mixture is covered and magnetically stirred until contents are completely dissolved. 50.0 g of sorbitol liquid (Fluka) is weighed in a 100 mL beaker then added to the hydroxypropyl methylcellulose solution (the 100 mL beaker is rinsed with water and the rinse added to the hydroxypropyl methylcellulose solution). 0.15 mL of peppermint flavor is added to the mixture with stirring followed by 0.25 mL of Antifoam 1510 (Dow Corning) with continued stirring for about 10 min. The solution is then transferred to a 500 mL volumetric flask and additional water for irrigation is added to bring the final volume to 500 mL. The final suspension vehicle is then sealed in screw capped bottles until ready for use.

To prepare the suspension containing Compound (I), the required amount of Compound (I) (for example 1-200 mg, particularly in micronized form) is first added to a fresh bottle. The bulk suspension vehicle is gently shaken then 10 mL of the vehicle is added to the bottle containing Compound (I). The bottle is then sealed and shaken vigorously to disperse the Compound, then left for about 1 minute before use. Alternatively, the desired amount of Compound (I) can be added to a fresh bottle containing 10 mL of the suspension vehicle, with the bottle then being sealed and shaken as previously described.

It will be understood, however, that a preferred composition of the present invention comprises Compound (I), or a pharmaceutically acceptable salt thereof formulated in a capsule or tablet.

Compound (I), or compositions comprising Compound (I) can be administered by any route which makes Compound (I) bioavailable, including oral and parenteral routes. For example, Compound (I), or compositions comprising Compound (I) can be administered orally, subcutaneously, intramuscularly, intravenously, transdermally, topically, intranasally, rectally, buccally, and the like. Alternatively, the compound may be administered by continuous infusion. It is understood, however, that oral administration is a preferred route of administration.

As used herein the term "effective amount" refers to the amount or dose of Compound (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications. While not to be construed as limiting the present invention in any way, 1-200 mg/day represents a typical effective amount of Compound (I).

Biological Activity:

Compound (I) possess a particular profile of activity in in vitro tests which suggests that it is particularly suitable for the treatment of inflammatory and immune disorders responsive to classical glucocorticoids. For example, in radio-labeled ligand binding studies carried out in HEK293 cells expressing human GR, MR, AR and PR, Compound (I) binds to GR with a Ki of less than about 0.50 nM. Furthermore, Compound (I) binds to GR with about 30 fold or more greater affinity relative to each of MR, AR, and PR. In whole cell glucocorticoid receptor-mediated transrepression assays, carried out in human skin fibroblast CCD-39 SK cells and U937 monocytes, Compound (I) is a potent and full transrepressor (greater than about 90% maximal inhibition) of the endogenous production of IL-6 and TNFα. Significantly, in a functional assay of GR-mediated transactivation, Compound (I) displays only partial agonist activity (less than about 50% maximal efficacy) in inducing GR/GRE-mediated gene transcription. Thus, Compound (I) displays a differentiated profile by inducing full GR-mediated transrepression, yet only partially inducing GR/GRE-mediated transactivation. Furthermore, in assays examining the effects on functional modulation of other steroid receptors, Compound (I) displays only limited activity in modulating gene expression mediated by AR, MR, and PR.

In both acute and chronic animal models of inflammation, comparing the effects of Compound (I) with a steroidal glucocorticoid, Compound (I) displays potent anti-inflammatory properties. For example, in an acute rat model of carrageenan-induced paw edema (CPE), Compound (I), upon oral administration, dose dependently inhibits carrageenan induced paw edema and inhibits production of interleukin-1-beta (IL-1β), a cytokine generated during the inflammatory response. These results compare favorably with the results elicited by prednisolone which was about 5 fold less potent under similar conditions.

Conversely, Compound (I) displays a reduced propensity for eliciting GR-mediated bone effects when examined in animal models of bone formation. For example, in a mouse serum osteocalcin assay comparing the effects of Compound (I) with prednisolone (at dosages approximating the respective ED50 values for Compound (I) and prednisolone in an animal model of inflammation), Compound (I) induces less reduction in the production of serum osteocalcin, a recognized marker of bone formation.

Typical procedures for the afore-mentioned in vitro assays and in vivo animal models are provided below. As used herein, "Kd" refers to the equilibrium dissociation constant for a ligand-receptor complex; "Ki" refers to the equilibrium dissociation constant for drug-receptor complex, and is an indication of concentration of drug that will bind to half the binding sites at equilibrium; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; and "ED50" refers to the dose of an administered therapeutic agent which produces 50% the maximal response for that agent.

Nuclear Hormone Receptor Binding Assays:

Cell lysates from human embryonic kidney HEK293 cells overexpressing human GR (glucocorticoid receptor), AR (androgen receptor), MR (mineralocorticoid receptor), or PR (progesterone receptor) are used for receptor-ligand competition binding assays to determine Ki values.

Briefly, steroid receptor competition binding assays are run in a buffer containing 20 mM Hepes buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 µg/mL aprotinin and 20 µg/mL leupeptin. Typically, steroid receptor binding assays include radio-labeled ligands, such as 0.3 nM [$^3$H]-dexamethasone for GR binding, 0.36 nM [$^3$H]-methyltrienolone for AR binding, 0.25 nM [$^3$H]-aldosterone for MR binding, and 0.29 nM [$^3$H]-methyltrienolone for PR binding, and either 20 µg 293-GR lysate, 22 µg 293-AR lysate, 20 µg 293-MR lysate or 40 µg 293-PR lysate per well. Assays are typically run in 96-well format. Competing test compounds are added at various concentrations ranging from about 0.01 nM to 10 µM. Non-specific binding is determined in the presence of 500 nM dexamethasone for GR binding, 500 nM aldosterone for MR binding, or 500 nM methyltrienolone for AR and PR binding. The binding reactions (140 µL) are incubated overnight at 4° C., then 70 µl of cold charcoal-dextran buffer (containing per 50 ml of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 µL of the binding reaction mixture is then transferred to another 96-well plate and 175 µL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 µM. The Kd for [$^3$H]-dexamethasone for GR binding, [$^3$H]-methyltrienolone for AR binding, [$^3$H]-aldosterone for MR binding, or [$^3$H]-methyltrienolone for PR binding, are determined by saturation binding. The IC50 values for compounds are converted to Ki using the Cheng-Prusoff equation.

Binding assay protocols similar to those described above can be readily designed by the ordinarily skilled artisan. Following procedures essentially as described above, Compound (I) displays the following receptor binding profile:

| GR Ki (nM) | AR Ki (nM) | MR Ki (nM) | PR Ki (nM) |
|---|---|---|---|
| 0.35 | 16.20 | 116.76 | 31.00 |

(Ki values represent a mean of 5 individual determinations)

To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art.

Nuclear Hormone Receptor Functional Modulation Assays:

Human embryonic kidney HEK293 cells are transfected with steroid hormone receptor and reporter gene plasmids using Fugene™ (Roche Diganostics) transfection reagent. Briefly, the reporter plasmid containing two copies of probasin ARE (androgen response element 5'GGTTCTTGGAGTACT3' (SEQ ID NO:1)) and TK(thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE (glucocorticoid response element 5'TGTACAGGATGTTCT'3 (SEQ ID NO:2)) and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 µM. In the antagonist mode for the assays, low concentrations of agonist for each respective receptor are added to the media (0.25 nM dexamethasone for GR, 0.3 nM of methyltrienolone for AR, 0.05 nM of promegestone for PR and 0.05 nM aldosterone for MR), and the ability of test compound to antagonize the agonist response is determined. After 24 hours of incubation with test compounds, cells are lysed and luciferase activity is determined using standard techniques.

Data are fitted to a four parameter-fit logistic curve fit to determine EC50 values. The percentage efficacy (compounds with saturated maximum responses) or the percent maximum stimulation (compounds with maximum responses that do not saturate) are determined relative to maximum stimulation obtained with the following reference agonists: 100 nM methyltrienolone for AR assay, with 30 nM promegestone for PR assay, with 30 nM aldosterone for MR assay and with 100 nM dexamethasone for GR assay. IC50 values may be determined similarly using antagonist mode assay data. Percent inhibitions may also be determined relative to the response in the presence of agonist alone, as described above.

Functional assays for nuclear hormone receptor modulation similar to those described above can be readily designed by the ordinarily skilled artisan. Following procedures essentially as described above, Compound (I) displays the following profile in activating transcription mediated by human GR, human AR, human MR and human PR:

| GR | | AR | | MR | | PR | |
|---|---|---|---|---|---|---|---|
| EC50 (nM) | % Eff.* | EC50 (nM) | % Eff.* | EC50 (nM) | % Eff.* | EC50 (nM) | % Eff.* |
| 1.9 | 45.7 | nd | 2.4 | nd | 8.5 | nd | 40.1 |

"nd" indicates values are greater than 10 µM
*percent efficacy at 10 µM (EC50 and % Efficacy values represent means of 3 individual determinations)

Glucocorticoid Receptor-Mediated Transrepression Assays:

1. IL-1β-Stimulated IL-6 Production in Human Skin Fibroblast CCD-39SK Cells:

Briefly, human skin fibroblast CCD-39SK cells (20,000 cells/well), obtained from the American Type Culture Collection (ATCC), Manassas, Va. U.S.A. (ATCC Catalog #CRL-1501) are seeded in 96-well plates in SF-GM (MEM) medium (ATCC Catalog #30-20030), supplemented with 10% fetal bovine serum (FBS), 100 U/mL penicillin, 100 μg/mL streptomycin and 2 mmol/L L-glutamine. Cells are maintained in a humidified chamber with 5% $CO_2$ at 37° C. Test compounds are added to the wells in various concentrations ranging from a final concentration of about 4.65 pM to 4.64 μM. 0.1 μM of dexamethasone is used as a positive control. 1-hour post treatment with test compound, IL-1β is added at final concentration of 1 ng/mL and the reaction mixture is incubated overnight. IL-6 concentrations are measured with an ELISA Kit (R&D Systems, Inc., Minneapolis, Minn., U.S.A.) using standard techniques. Briefly, take 10 μL of supernatant from each well and add 90 μL of assay buffer. IL-6 concentrations are quantified by reading absorbance at 450 nm. A standard curve of absorbance versus IL-6 concentration is constructed and used to determine the concentration of IL-6 in experimental samples.

2. LPS-Stimulated TNF-α Production in PMA-Differentiated U937 Cells:

Human U937 pre-monocytic cells (ATCC Catalog #CRL-1593.2) are grown in complete RPMI 1640 medium (ATCC Catalog #30-2001) containing 10% fetal bovine serum (FBS). To allow monocytes to differentiate to adherent macrophages, U937 cells are washed in PBS (Calcium, magnesium-free) and resuspended in fresh RPMI medium containing 20 nM phorbol 12-myristate-13-acetate (PMA) overnight. After differentiation, test compounds are added to the cells in the 96-well plate at various concentrations ranging from about 4.65 μM to 4.64 μM. 1-hour post treatment with test compound, LPS is added at final concentration of 100 ng/mL and the reaction mixture is incubated overnight.

TNF-α production is measured with an ELISA kit (R&D Systems, Inc., Minneapolis, Minn., U.S.A.) using standard techniques. Briefly, 25 μL cell-free supernatant is transferred to another 96-well plate and 75 μL of assay buffer is added. TNF-α is quantified by reading absorbance at 450 nm. A standard curve of absorbance versus TNF-α concentration is constructed and used to determine the concentration of TNF-α in experimental samples.

Following procedures essentially as described above, Compound (I) induces about 90% or more maximal inhibition of the endogenous expression of IL-6 and TNF-α with EC50 values of about 4.8 and 30 nM, respectively (with data from IL-6 assay representing a mean of 22 individual determinations; and data from TNF-α assay representing a mean of 6 individual determinations)

Animal Models:

1. Carrageenan-Induced Paw Edema (CPE) Model

Carrageenans are a group of polysaccharides which can induce an acute inflammatory response in animals. Cardinal signs of inflammation including edema, hyperalgesia and erythema are developed in the injection site immediately following injection. The CPE model (Winter et al., *Proc. Soc. Exp. Biol. Med.* 111, 544-547, 1962) is a recognized model of inflammation and can be used to evaluate the antinflammatory effects of glucocorticoid receptor ligands.

To evaluate the anti-inflammatory effects of Compound (I), the Compound (I) is formulated in a vehicle comprising 0.5% carboxymethyl cellulose and 0.25% Tween 80 then administered orally via gavage to male Sprague-Dawley rats (180-200 g) (Harlan Industries, Indianapolis, Ind.). For comparison, prednisolone is administered orally in the same vehicle. Two hours later, 1% carrageenan in 50 μL of 0.9% pyrogen free saline is injected into the subplantar regions of the right hind paw. Rats are euthanized by $CO_2$ at 3 hours after the carrageenan injection. Paws are removed then weighed using a microbalance. Paws are then immediately immersed into liquid nitrogen until frozen. Frozen paws are dissected by making several cuts on the paw surface then centrifuged to extract the exudates. Exudate levels of IL-1β, a cytokine generated during the inflammatory response, is then measured by ELISA (R&D Systems, Inc., Catalog No. RLB00) using standard techniques. Total paw protein is also measured using a protein assay kit (Pierce Biotechnology, Inc., Rockford, Ill., U.S.A., Catalog No. 1856210) and the absolute level of IL-1β is normalized to yield a concentration value of ng IL-1β/mg total protein.

Compound (I) inhibits carrageenan induced paw weight gain with an ED50 of about 1.2 mg/kg. Compound (I) also reduces Paw exudate levels of IL-1β with an ED50 of about 0.31 mg/kg. Conversely, prednisolone treatment in this model inhibits paw weight gain with an ED50 of about 6.6 mg/kg, and reduces IL-1β levels with an ED50 of less than about 1 mg/kg (with ED50 values representing a mean of 5 individual determinations).

2. Serum Osteocalcin Assay

Bone loss/osteoporosis and the resulting increased risk of fracture is a common and significant adverse effect that results from glucocorticoid therapy. Glucocorticoid induced osteoporosis is believed to result, at least in part, from an inhibition of bone formation. The measurement of serum osteocalcin, a biological marker of bone synthesis, is a recognized tool for assessing the adverse effects of glucocorticoid therapy on bone. (see Pearce et al., *J. Clin. Endocrino. Metab.* 83: 801-806, (1998)).

To assess the effects of Compound (I) on bone formation, Compound (I) is formulated in a vehicle comprising 5% carboxymethyl cellulose and 0.25% Tween 80 and administered orally via gavage to sixteen week old male Swiss-Web mice (Harlan Industries, Indianapolis, Ind.) for seven days. For comparison, prednisolone is administered orally in the same vehicle. Serum is collected 24 hours after the last dose and osteocalcin levels are determined using a competitive radioimmunoassay (RIA) kit (Biomedical Technologies, Inc., Stoughton, Mass.) modified to a 96 well format. Briefly, each well of a Multiscreen™ plate (MAHV N45, Millipore, Bedford, Mass.) containing 2.5 μL mouse serum, 2.5 μL goat anti-mouse osteocalcin, 0.625 μL normal goat serum, and 119.375 μL RIA buffer (0.1225 M NaCl, 0.01 M $NaH_2PO_4$, pH 7.4, 0.025 M tetra sodium EDTA, 0.1% (w/v) BSA, and 0.1% (w/v) Tween-20) is incubated at 4° C. for 18 h on an orbital shaker at 80 rpm. Following the addition of 0.2 μCi/ml [$^{125}$I] mouse osteocalcin in 25 μl RIA buffer to each well, the plates are incubated for 24 h at 4° C. on an orbital shaker at 80 rpm. The complex is precipitated for 2 h at 25° C. by the addition of donkey anti-goat IgG (1:30) in 0.2 M $Na_2HPO_4$, pH 7.4, 5% (w/v) polyethylene glycol, 125 μL/well. The precipitate is collected by vacuum filtration and washed once with 100 μL/well $dH_2O$. The filters are punched and the radioactivity quantitated on a gamma counter (Cobra II, Packard Instruments, Meriden, Conn.). Radioactivity detected on the filters from test samples is inversely proportional to serum osteocalcin concentration. A standard curve of purified mouse osteocalcin is used to calculate the serum osteocalcin concentration in test samples.

Comparing daily dosages approximating the ED50 values determined in the rat CPE model (1 mg/kg/day Compound (I)

and 10 mg/kg/day prednisolone), Compound (I) induces less reduction in serum osteocalcin levels than prednisolone (with serum osteocalcin levels representing a mean of 6 individual determinations).

As stated, Compound (I) possess additional technical effects or advantageous properties which address other limitations in the field of patient therapy and pharmaceutical development. For example, Compound (I) displays good bioavailability and good plasma exposure following oral administration to test animals. In addition, Compound (I) shows only minor metabolism when incubated with human hepatocyte cultures in vitro. Further, metabolic profiling of rat, dog and monkey plasma, following in vivo administration of Compound (I), showed that Compound (I) was the major circulating entity, with no metabolites detected in monkey plasma. Furthermore, Compound (I) appears to be non-genotoxic when examined in in vitro assays and in vivo studies of genotxic potential. In view of these and other properties, Compound (I) is believed to be especially suitable for the treatment of chronic inflammatory or immune disorders which often require repeat or long term dosing of the therapeutic agent.

In addition to properties which benefit patient therapy, Compound (I) possesses yet additional advantages which facilitate its pharmaceutical development. For example, Compound (I) is capable of isolation in crystalline form. It will be appreciated that in addition to possessing desired biological properties, it is also desirable for a therapeutic agent to possess certain physical characteristics as well. In particular, compounds which are stable, crystalline solids are desired as they are particularly amenable to conventional paradigms of chemical synthesis, purification, storage, and formulation or dosage form development. "Crystalline form" or "crystal form" as used herein refers to a solid form of a chemical species which has a distinct crystal arrangement that distinguishes the solid form from other forms of the same elemental composition. "Substantially pure crystalline form", as used herein, refers to pure crystal form of the chemical species comprising greater than about 95% of the particular crystalline form, and preferably greater than about 98% of the particular crystalline form.

A particular crystal form can be characterized and thus distinguished from other solid forms of the same chemical species using conventional techniques, including X-ray powder diffraction (XRPD), spectroscopic methods (e.g, infrared (IR) or nuclear magnetic resonance (NMR) spectroscopy), and thermal techniques (e.g differential scanning calorimetry (DSC), thermal gravimetric analysis (TGA), or differential thermal analysis (DTA)). While XRPD is a particularly useful means for characterizing crystal forms of a chemical species, it will be appreciated that the actual peak intensities in the X-ray pattern may vary from analysis to analysis of the same crystal form depending on the sample analyzed and the instrument, solvent, or procedures employed. In addition, it will also be understood that while the exact peak locations obtained from analysis of a given crystal form, as measured in ° 2θ, may vary from analysis to analysis (for example ±0.1°), the relative pattern of peak locations will remain essentially the same between spectra.

The present invention provides Compound (I) in crystalline form. More particularly, the present invention provides the free base of Compound (I) in crystalline form having characteristic peaks at ° 2θ of about 10.9, 18.8, and 22.9 (Form I in the Examples herein). In addition, the present invention provides the free base of Compound (I) in crystalline form having characteristic peaks at °2θ of about 4.5, 9.0, 11.5, and 14.7 (Form II in the Examples herein). More particularly still, the present invention provides each of Forms I and II of Compound (I) in substantially pure crystalline form. In addition, Compound (I) is non-hygroscopic and stable under conditions of increased temperature, relative humidity, and light exposure.

One of skill in the art will also appreciate that particle size can affect the in vivo dissolution of a pharmaceutical agent which, in turn, can affect absorption of the agent. "Particle size" as used herein, refers to the diameter of a particle of a pharmaceutical agent as determined by conventional techniques such as laser light scattering, laser diffraction, Mie scattering, sedimentation field flow fractionation, photon correlation spectroscopy, and the like. Where pharmaceutical agents have poor solubility, small or reduced particle sizes may help dissolution and, thus, increase absorption of the agent. Amidon et al., *Pharm. Research,* 12; 413-420 (1995). Methods for reducing or controlling particle size (micronization) are conventional and include ball milling, pin milling, jet milling, wet grinding, and the like. Another method for controlling particle size involves preparing the pharmaceutical agent in a nanosuspension.

It has been discovered that chemical preparations of Compound (I) yield crystals having particular particle sizes. In particular, samples of the free base of Compound (I), when prepared essentially according to Example 1(a) as described herein, provide an average particle size of less than 20 μm and a $d_{90}$ particle size (i.e. the size of which 90% of the particles are smaller than or equal to) of less than 50 μm (particle sizes determined using a Beckman Coulter LS13 320 Laser Diffraction Particle Size Analyzer). In addition, micronized samples of the free base of Compound (I), when prepared essentially as described in Examples 6 and 7 herein, provide an $x_{50}$ particle size (i.e. the size of which 50% of the particles are smaller than or equal to) of less than 10 μm and an $x_{90}$ particle size (i.e. the size of which 90% of the particles are smaller than or equal to) of less than 20 μm (particle sizes determined using a Sympatec (HELOS Particle Size Analysis system) laser diffraction particle size analyzer). As such, a particular embodiment of the present invention is the free base of Compound (I), or a pharmaceutical composition comprising the free base of Compound (I), wherein Compound (I) has an average particle size less than 20 μm and a $d_{90}$ particle size of less than 50 μm. A more particular embodiment is the free base of Compound (I), or a pharmaceutical composition comprising the free base of Compound (I), wherein Compound (I) has an average particle size less than 15 μm and a $d_{90}$ particle size of less than 40 μm. Even more particular is the free base of Compound (I), or a pharmaceutical composition comprising the free base of Compound (I), wherein Compound (I) has an $x_{50}$ particle size of less than 10 μm and an $x_{90}$ particle size of less than 20 μm. More particular still is the free base of Compound (I), or a pharmaceutical composition comprising the free base of Compound (I), wherein Compound (I) has an $x_{50}$ particle size of less than 5 μm and an $x_{90}$ particle size of less than 15 μm. In addition, an example of Compound (I) in nanosuspension is provided in the Examples, herein.

Methods for preparing Compound (I) are known in the art. For example, WO 04/052847 provides general procedures which may be employed. Furthermore, WO 05/066161 provides additional general procedures which may be employed. The following Schemes, Intermediates, and Examples further illustrate the invention and represent typical syntheses of Compound (I). The reagents and starting materials are readily available to, or may be readily synthesized by, one of ordinary skill in the art. It should be understood that the Schemes, Intermediates, and Examples are set forth by way of illustration and not limitation, and that modifications may be made by one of ordinary skill in the art.

As used herein "DMSO" refers to dimethyl sulfoxide; "DIAD" refers to diisopropyl azodicarboxylate; "ADDP" refers to 1,1'-(azodicarbonyl)dipiperidine; "THF" refers to tetrahydrofuran; "DMF" refers to dimethyl formamide; "TMSCN" refers to trimethylsilyl cyanide; "TEA" or "Et$_3$N" refers to triethylamine; "DME" refers to 1,2-dimethoxyethane; "AcOEt" refers to ethyl acetate; "pyr" refers to pyridine; "MsCl" refers to methanesulfonyl chloride "Et$_2$NH" refers to diethylamine; "MeOH" refers to methanol; "PhCH$_3$" refers to toluene; "PhH" refers to benzene; "PBu$_3$" refers to tributylphosphine; "PPh$_3$" refers to triphenylphosphine; "dppf" refers to 1,1'-bis(diphenylphosphanyl)ferrocene, "NaO-t-Bu" refers to sodium tert-butoxide; "MTBE" refers to tert-butyl methyl ether.

Scheme I

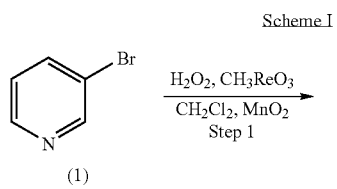

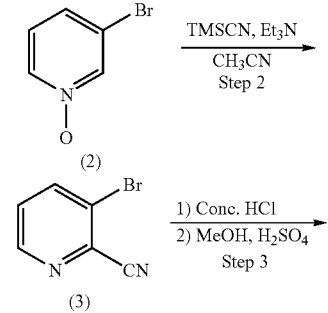

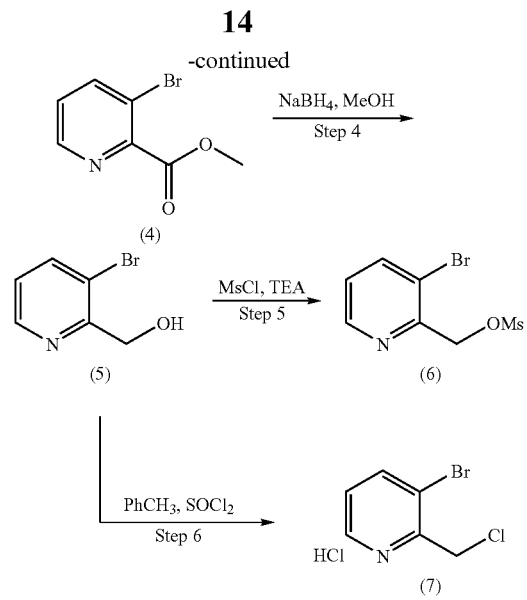

In Scheme I is described the preparation of pyridine intermediates (5), (6), and (7). In Scheme I, Step 1,3-bromopyridine (1) is oxidized to 3-bromo-pyridine-N-oxide (2). In Scheme I, Step 2, cyanide substitution gives 3-bromo-pyridine-2-carbonitrile (3). The nitrile of formula (3) is hydrolyzed in Step 3 to the carboxylic acid and esterified with acid catalysis to the ester of formula (4). In Scheme I, Step 4, the ester is reduced to the pyridinylmethanol of formula (5) using sodium borohydride. The pyridinylmethanol is converted to the mesylate of formula (6) with methanesulfonyl chloride (Step 5) or to the pyridinylmethyl chloride of formula (7) using thionyl chloride (Step 6).

Scheme II

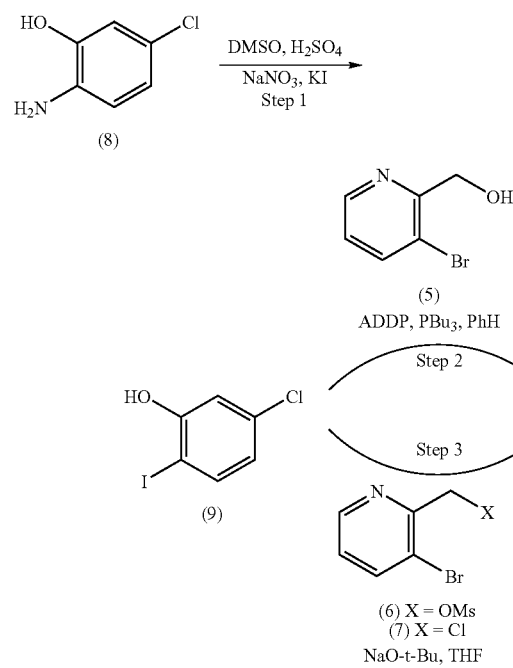

-continued

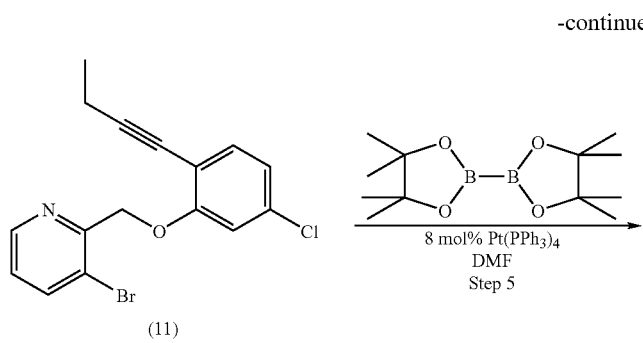

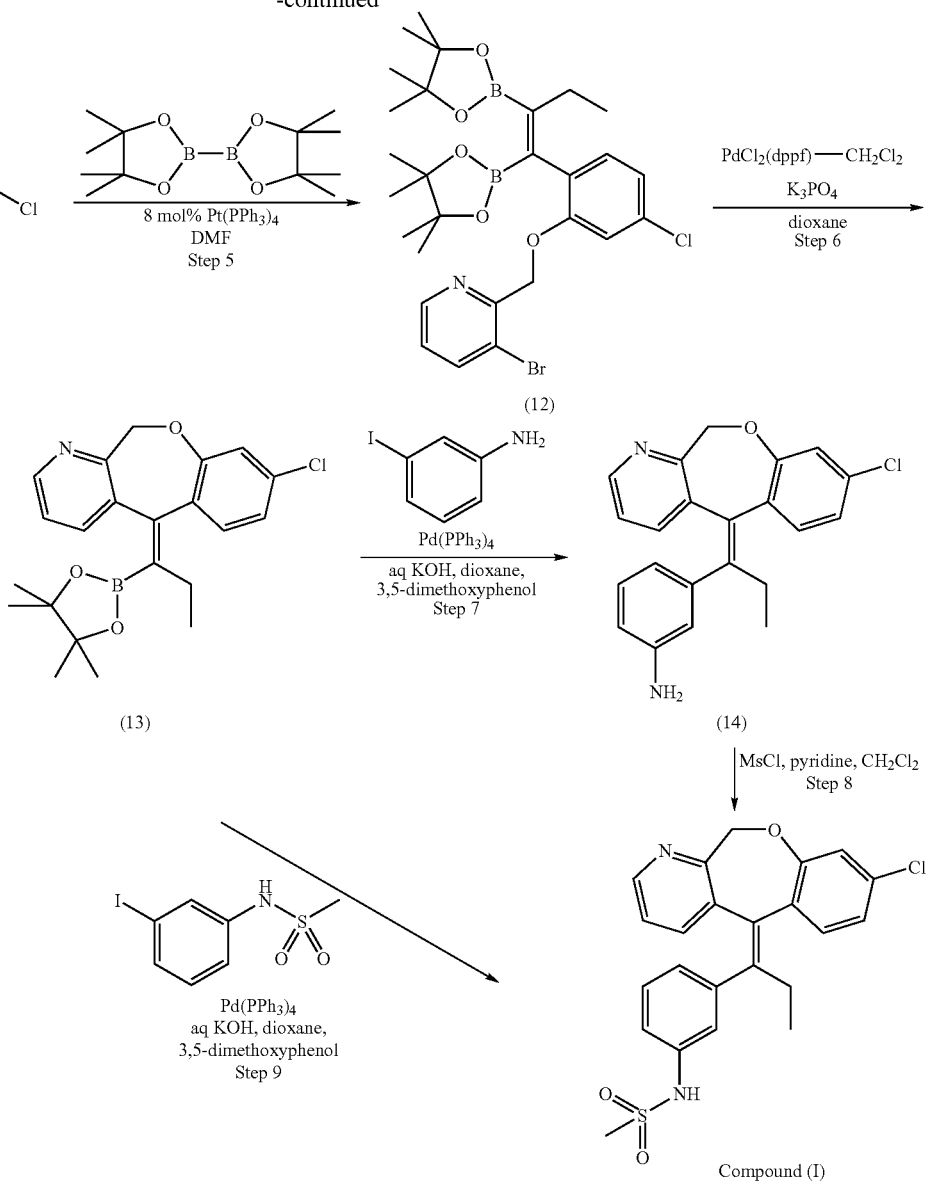

Compound (I)

In Scheme II is described the synthesis of the final benzopyridyl-10-oxepine of Compound I. In Scheme II, Step 1, a modified Sandmeyer reaction of an aniline of formula (8) gives 5-chloro-2-iodophenol of formula (9).

In Scheme II, Step 2, a Mitsunobu reaction between 5-chloro-2-iodophenol and a pyridinylmethanol of formula (5) gives the iodoaryl ether of formula (10). Other suitable reagents include DIAD and triphenylphosphine in THF. Alternatively, in Step 3, the iodoaryl ether of formula (10) is accessed by means of alkylation with a pyridinemethyl mesylate or chloride of formula (6) or (7) using a base such as sodium t-butoxide, potassium t-butoxide, or potassium carbonate in an inert solvent such as THF or acetonitrile.

In Scheme II, Step 4 the iodoaryl ether of formula (10) is treated with 1-butyne in a Sonagashira coupling to provide the alkynylaryl ether of formula (11). The reaction is performed using a mixture of diethylamine/acetonitrile/THF; and 1-butyne is bubbled into the reaction mixture. Alternatively, the reaction is performed using triethylamine as base and treated with 24% wt/wt solution of 1-butyne in DMF.

In Scheme II, Steps 5 and 6, platinum-catalyzed diboronation of the alkynylaryl ether of formula (11) gives a diboronic ester of formula (12) which forms a vinyl boronic ester of formula (13) upon an intramolecular Suzuki coupling.

In Scheme II, Step 7, an intermolecular Suzuki coupling between vinyl boronic ester (13) and 3-iodoaniline affords the aniline of formula (14). In order to improve purification of the aniline of formula (14), the aniline may be treated with an appropriate acid to form a salt. For example, the aniline of formula (14) may be treated with toluenesulfonic acid to provide the aniline of formula (14) as the ditoluenesulfonic acid salt.

In Scheme II, Step 8, the aniline is sulfonylated with methanesulfonyl chloride to give the final benzopyridyl-10-oxepin of Compound (I). Alternatively, in Scheme II, Step 9, the benzopyridyl-10-oxepin of Compound (I) is accessed directly by performing the Suzuki coupling with N-(3-iodophenyl)-methanesulfonamide. Compound (I) may be purified by recrystallization from, for example, methanol.

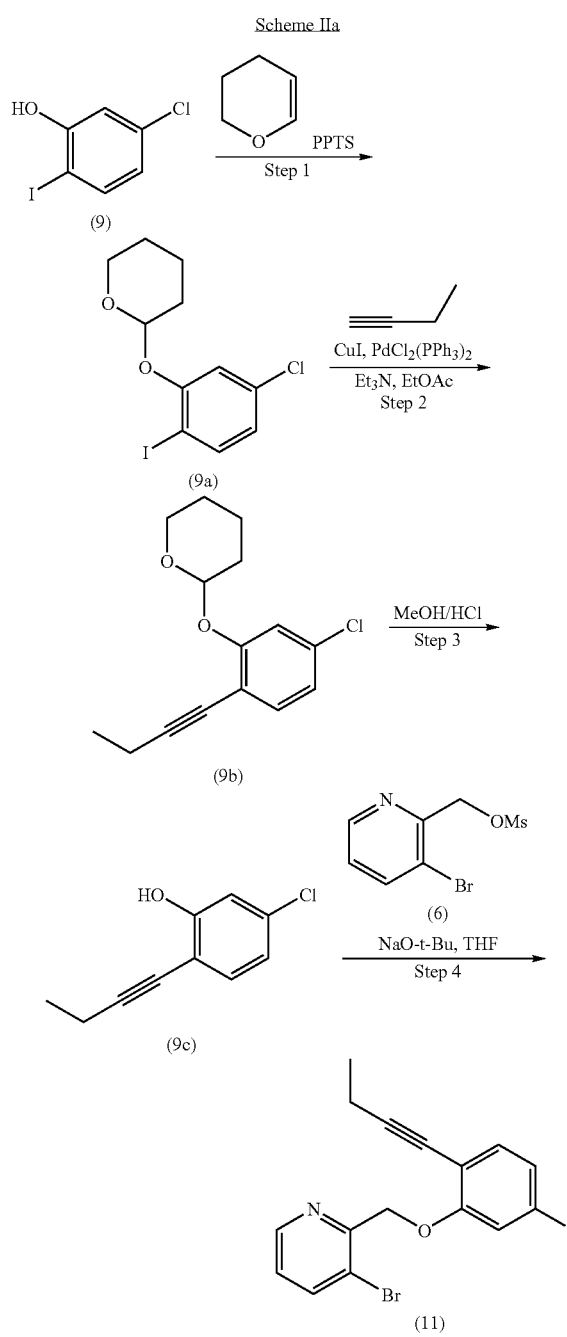

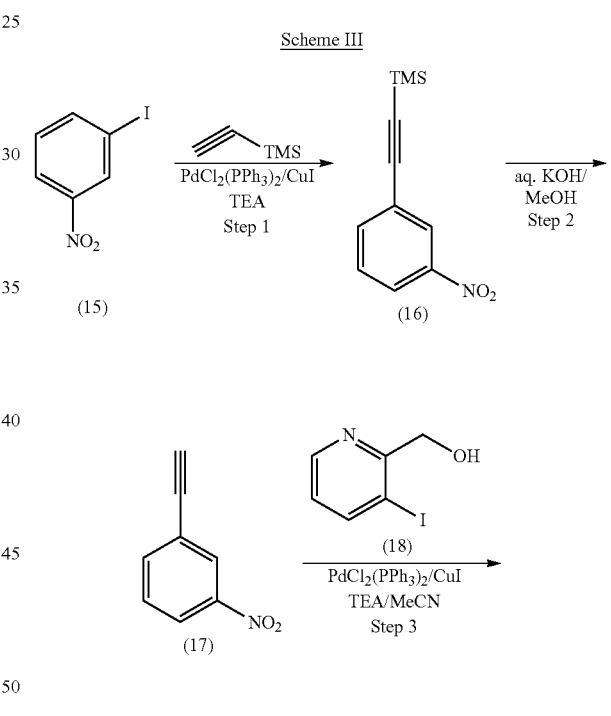

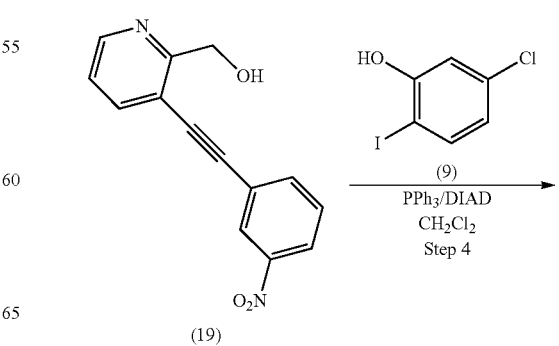

(triphenylphosphine)palladium (II), and copper (I) iodide. 1-Butyne is added at a temperature of about 0 to 10° C. and the reaction performed for about 10 to 24 h at about room temperature. After workup the product may be purified by silica gel chromatography and recrystillization from heptane/triethylamine.

In Step 3, the THP ether of formula (9b) is deprotected using acidic conditions to the alkynylphenol of formula (9c). Particular conditions use a catalytic amount of a mineral acid, such as hydrochloric acid, in an alcoholic solvent such as methanol. The reaction is performed for 30 min to 6 h at 0° C. to room temperature.

In Scheme IIa, Step 4, the alkynylphenol of formula (9c) is alkylated with a pyridinemethyl mesylate of formula (6), using a base such as sodium t-butoxide, potassium t-butoxide, or potassium carbonate in an inert solvent such as THF or acetonitrile. Particular conditions use sodium t-butoxide in THF which is added to a solution of the mesylate and phenol at a temperature below 0° C., and subsequently stirred at room temperature for 24 to 72 h. After extractive workup the product is recrystillized from ethanol.

In Scheme IIa is described an alternate synthesis of the alkynylaryl ether of formula (11).

In Scheme IIa, Step 1, 5-chloro-2-iodophenol of formula (9) is protected as the tetrahydropyran (THP) ether of formula (9a). The reaction is performed in an inert solvent such as dichloromethane, in the presence of an acid catalyst, such as pyridinium p-toluenesulfonate. 3,4-Dihydro-2H-pyran is added at or below about 30° C. and then the reaction performed for 10 to 24 h at about room temperature.

In Scheme IIa, Step 2, the iodobenzene of formula (9a) is treated with 1-butyne in a Sonagashira coupling to provide the alkynyl benzene of formula (9b). The reaction is performed using triethylamine with an inert solvent, such as ethyl acetate, and a palladium catalyst, such as dichlorobis

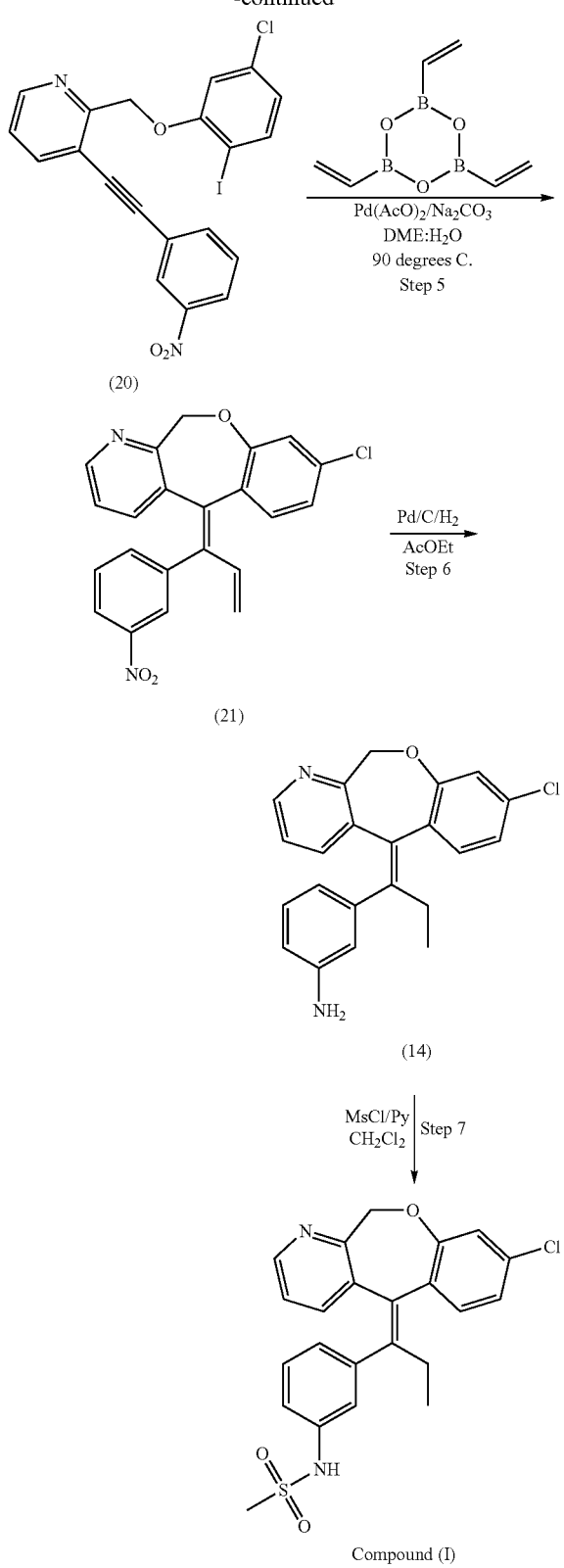

Compound (I)

In Scheme III is described an alternative synthesis of the final benzopyridyl-10-oxepine of Compound (I). In Scheme III, Step 1, a Sonagashira reaction between trimethylsilyl-(acetylene) and 3-iodonitroaniline of formula (15) affords trimethylsilyl alkyne of formula (16) which, upon desilylation, is converted to the alkyne of formula (17) in Scheme III, Step 2

In Scheme III, Step 3, using typical Sonagashira reaction conditions, (17) is coupled with pyridinylmethanol of formula (18) to give the diaryl alkyne of formula (19). In Scheme III, Step 4, a Mitsonobu reaction between the diaryl alkyne (19) and 5-chloro-2-iodophenol of formula (9) affords the biaryl alkynyl iodoaryl ether of formula (20). Typical conditions include triphenylphosphine and DIAD in methylene chloride.

In Scheme III, Step 5, biaryl alkynyl iodoaryl (20) is converted to pyridyl oxepine of formula (21) in the presence of trimeric vinyl boronic anhydride via a palladium-catalyzed intramolecular Heck-Suzuki cascade reaction. Optimized conditions include slow addition of the boronic anhydride to a mixture of biaryl alkynyl iodoaryl (20), 2 mol % palladium (II) acetate, 2 equiv of sodium carbonate in 4:1 by vol of DME:water at 90° C.

In Scheme III, Step 6, a one-pot hydrogenation on Pd/C of both the double bond and nitro group of pyridyl oxepine (21) yields the aniline of formula (14). In Scheme III, Step 7, the aniline is sulfonylated with methanesulfonlyl chloride using pyridine base to give the final benzopyridyl-10-oxepine of Compound (I).

Instrumental Analysis

GC-MS analysis may be carried out on an HP 6890 Series GC-MS (70 eV) equipped with an Agilent 0.25-mm×15-m× 0.25 μm capillary column using temperature programming (60-280° C. in 7.3 min then 280° C. for 2 min) LC-MS analysis may be performed on an Agilent 1100 Series HPLC using a Waters Xterra™ MS $C_{18}$ 4.6-mm×50-mm 3 5-μm column and atmospheric pressure chemical ionization (APCI). Typically the analysis is conducted using 80% methanol:water to 100% methanol gradient. Alternatively LC-MS analysis may be performed on a Waters XTerra C18 2.1×50 mm 3 5 μm column and electrospray ionization. Solvent system is 5-100% acetonitrile/MeOH (50/50) with 0.2% $NH_4$ formate. $^1H$ NMR spectra may be recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. X-ray powder diffraction (XRPD) patterns may be obtained on a Bruker D8 Advance XRPD powder diffractometer, equipped with a CuKα source (λ=1.54056 angstrom) and an electronic solid-state detector, operating at 40 kV and 40 mA. Each sample is scanned between 4° and 40° in °2θ, with a step size of 0.02° in 2θ and a scan rate of 3 second/step, with controlled variable (v12) divergence and receiving slits and a 0.2 mm detector slit. Alternatively, X-ray powder diffraction analysis may be performed using a Bruker D8 Advance diffractometer, with samples being scanned between 2° and 45° in °2θ, with a step size of 0.02° in 2θ and a scan rate of 5 second/step, with 0.6 mm divergence slit, 0.6 mm anti-scatter slit, 0.1 mm receiving slit and a 0.6 mm detector slit. Differential scanning calorimetry (DSC) analyses may be carried out on a Mettler-Toledo DSC unit (Model 822). Samples are heated in closed aluminum pans with pinhole from 30 to 300° C. at 5° C./min with a nitrogen purge of 50 mL/min. Differential thermal analyses (DTA) and thermogravimetric analysis (TGA) may be carried out on a Mettler Toledo DTA and TGA unit (Model TGA/SDTA 851). Samples are heated in sealed aluminum pans with a pinhole from 25 to 300-350° C. at 10° C./min with a nitrogen purge of 50 ml/min. The TGA temperature is calibrated with indium/aluminum standard, m.p.=156.6 and 660.3° C. Weight calibration is performed with manufacturer supplied standards and verified against sodium citrate dehydrate desolation. The names of the compounds of the present invention are generally obtained from ChemDraw Ultra™, version 7.0.1.

Intermediate 1

5-Chloro-2-iodo-phenol

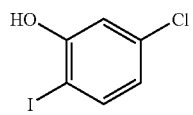

2-Amino-5-chlorophenol (5.7 g, 40 mmol) is dissolved in DMSO/water/H$_2$SO$_4$ (200/60/140 mL) and cooled to 0° C. To this solution is added sodium nitrite (4.1 g, 60 mmol) in water (20 mL) and the mixture is stirred for 1 h at 0° C. To the mixture is added potassium iodide (19.9 g, 120 mmol) in water (20 mL) and the mixture is stirred at room temperature for 1 h. Another batch of potassium iodide (19.9 g, 120 mmol) in water (20 mL) is added and the mixture is stirred at room temperature for 1 h. The mixture is diluted with ethyl acetate, washed with water, saturated aqueous sodium sulfate, and brine. The organic portion is dried over MgSO$_4$, filtered, and concentrated under reduced pressure. The resulting residue is purified by flash chromatography (Biotage™ Si65M, 20% ethyl acetate/hexane) to yield 8.09 g (79%) of the title compound as a pink solid. GCMS m/e 254 [M]$^-$.

Alternate Procedure:

A 50 L three neck round bottom flask is equipped with a mechanical stirrer, addition funnel, nitrogen inlet, drying tube and thermocouple placed in a cooling tub. Water (4.5 L) is charged to the flask, stirring is initiated, and the reaction is cooled to 0° C. Sulfuric acid (3.7 L) is added dropwise maintaining the temperature ≦30° C. 2-Amino-5-chlorophenol (1500 g) is charged to the flask maintaining the temperature ≦30° C. over 20 min. DMSO (12 L) is added dropwise maintaining the temperature ≦30° C. over one hour. The reaction mixture is cooled to −5 to 0° C. A solution of sodium nitrite (1082 g) in water (6 L) is added dropwise maintaining the temperature ≦0° C. over one hour and 45 min. After the addition is complete, the reaction mixture is stirred for a minimum of one hour at a temperature of ≦0° C. A 50 L three neck round bottom flask is equipped with a mechanical stirrer, addition funnel, nitrogen inlet, and thermocouple placed in a heating mantle. Potassium iodide (6.9 kg) and water (7.5 L) are charged to the flask, stirring is initiated and the reaction heated to 48 to 50° C. 2-Amino-5-chlorophenol diazotized solution is charged to the flask in portions maintaining the temperature at 48 to 50° C., using two condensers to vent the gases. The reaction mixture is heated for 2 h at 48 to 50° C. After this time the heating is stopped and the reaction is stirred at ambient temperature overnight. The reaction progress is monitored by TLC (heptane:EtOAc, 9:1). The starting material is observed at R$_f$=0.3 and product at R$_f$=0.6. The reaction is deemed complete when no starting material is observed. Once the reaction is complete, the reaction mixture is diluted with MTBE (16 L) and stirred for 20 min. The reaction mixture is transferred to a separatory funnel and the organic layer is separated from the aqueous layer. The organic layer is washed with a solution of Na$_2$S$_2$O$_3$ (3 kg) and water (12 L) and stirred for 5-10 min. The organic layer is separated and the same washing sequence repeated twice more. The organic layer is separated from the aqueous layers and all aqueous washes are discarded. The organic layer is washed with a saturated aqueous sodium bicarbonate solution (4 L). The organic layer is separated from the aqueous layer and the organic layer is washed with brine (4 L). The organic layer is separated and dried over magnesium sulfate, treated with charcoal, filtered, and concentrated. The resulting residue is co-evaporated with heptane (1 L) using an oil pump to remove residual solvents. The residual brown oil (2880 g) is dissolved in heptane (1 mL/g) and the solution is placed in a freezer overnight. The solids are collected by filtration, washed with cold heptane (2×600 mL, 0° C.), and dried in a vacuum oven at ambient temperature overnight. Tan solids are obtained.

Intermediate 2

3-Bromo-pyridine 1-oxide

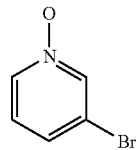

Methyltrioxorhenium (100 mg, 0.401 mmol) is dissolved in dichloromethane (40 mL) and 3-bromopyridine (15.8 g, 100 mmol) is added followed by 30% aqueous H$_2$O$_2$ (22.7 mL). The biphasic mixture is stirred at room temperature. After 18 h MnO$_2$ (25 mg, 0.29 mmol) is added and the mixture is stirred at room temperature for 2 h. The mixture is extracted with dichloromethane and the combined extracts are washed with brine, dried over MgSO$_4$, filtered, and concentrated under reduced pressure to yield 9.52 g (55%) of the title compound as an orange oil. GCMS m/e 174 [M−H]$^-$.

Alternate Procedure:

A 22 L three-neck round bottom flask is equipped with a mechanical stirrer and thermocouple. The flask is charged with 3-bromopyridine (3169 g, 20 mol), dichloromethane (8.2 L) and methyltrioxorhenium (10 g). The reaction mixture is cooled to 18° C. using a cold tap water bath and 30% aqueous hydrogen peroxide solution (3.07 L, 30 mol) is added in portions over about 15 min. The reaction is slightly exothermic and ice is added to the cooling tub in order to maintain the temperature at 20-25° C. The reaction mixture is allowed to stir overnight in a bath at room temperature (do not empty the bath). The reaction progress is monitored by TLC (heptane:EtOAc, 1:1) Starting 3-bromopyridine is observed to have an R$_f$=0.6 and product R$_f$=0.1. Traces of starting material may be present after overnight stirring and the reaction can either be worked up or stirred for an additional 8-24 h. Once the reaction is deemed complete, manganese dioxide (31 g, <10 microns) is added in small portions at a rate to control foaming and maintain the temperature at 20-25° C. Ice may be added to the cooling water tub if the temperature goes higher. If foaming is observed, more manganese dioxide may be added. When no more foaming is observed after addition of a fresh portion of manganese dioxide, solid sodium chloride (860 g) is added and the reaction mixture is stirred for an additional 30 min at room temperature. The reaction mixture is transferred to a separatory funnel and the organic layer is separated. The aqueous layer is extracted with dichloromethane (3×2.5 L). The extractions from each organic layer may be monitored using TLC. If product is present after last extraction, the aqueous layer may be filtered, then additional sodium chloride (500 g) may be added, and the mixture stirred to dissolve the salt. The aqueous layer is then extracted with dichloromethane (3×2 L). The combined organic portion is dried over magnesium sulfate, filtered, and concentrated. A pale yellow oil resides in the flask. This material may be used directly to prepare the 3-bromopyridine-2-carbonitrile.

Intermediate 3

3-Bromo-pyridine-2-carbonitrile

3-Bromo-pyridine 1-oxide (9.4 g, 54 mmol) is dissolved in acetonitrile (60 mL) and triethylamine (15 mL) is added followed by trimethylsilyl cyanide (21.7 mL, 163 mmol). The mixture is heated to 100° C. and stirred for 16 h. The mixture is cooled to 0° C., poured into 250 mL of 5 M aqueous NaOH, and extracted with dichloromethane. The combined extracts are washed with brine, dried over $MgSO_4$, filtered, and concentrated under reduced pressure. The resulting material is purified using flash chromatography (Biotage® Si65M, 20% ethyl acetate/hexane) to yield 7.8 g (79%) of the title compound as a yellow solid. GCMS m/e 182, 184 $[M]^-$.
Alternate Procedure:
A 50 L three-neck round bottom flask is equipped with a mechanical stirrer, thermocouple, nitrogen inlet, efficient reflux condenser, and drying tube (do not set up drying tube during addition of trimethyl silylcyanide). The flask is charged with 3778 g (about 20 mol) crude 3-bromopyridine-N-oxide (prepared, for example, essentially as described in the Alternate Procedure for Intermediate 2), acetonitrile (19 L) and triethylamine (6.667 L, 50 mol). The reaction mixture is heated to a gentle reflux of about 70-73° C., then neat trimethyl silylcyanide (6.667 L, 50 mol) is added via the addition funnel in 10-15 minute intervals, over a total of 3 h. After addition of each portion of trimethyl silylcyanide, the reaction proceeds toward strong reflux (if vapors escape, additional trimethylsilylcyanide may be needed to drive the reaction to completion). Once the addition is complete, the reaction mixture is stirred at reflux for 20 h with adjustment of heating rate as necessary to maintain the reflux. The reaction progress is monitored by TLC (heptane EtOAc 1:1). Once the reaction is deemed complete the reaction mixture is cooled to 0-10° C. A solution of 50% aqueous NaOH (7.2 kg) in water (9 L) is added in a stream over 30 min and an exotherm results. The temperature rises to 20-25° C. and the reaction is stirred for 30 min at 15-25° C. The reaction mixture is transferred to a separatory funnel and the organic layer is separated. The organic layer is washed with brine (4 L) and the combined aqueous layers are extracted with EtOAc (3×3 L). The combined organic layers are washed with brine (3 L), treated with charcoal, dried over magnesium sulfate, filtered, and concentrated. The resulting solids (about 3.8 kg) are dissolved in EtOAc (25 L, using some heat), dried over magnesium sulfate, charcoal, filtered and concentrated. The resulting tan/ brown solids are dissolved in ethanol (7 L) with heating. The resulting solution is transferred to a pail and allowed to stand at room temperature overnight. After this time the solids are collected by filtration and washed with cold ethanol on a filter (2×1 L, −20° C.). The solids are dissolved in EtOAc (20 to 25 L), the solution dried over magnesium sulfate, treated with charcoal to remove the color, and then filtered. The filter cake is washed with EtOAc (2×2 L) and the filtrates combined and concentrated to dryness. The residual solids (2.7 kg) are co-evaporated with EtOH (1 L). Then the solids are dissolved in EtOH (6 L) using heating. A clear solution forms at about 70° C. and the solution is then cooled to 0-5° C. and stirred for 2 h at this temperature. The solids are collected by filtration, washed with cold ethanol (2×1 L, 0-5° C.), and then heptane (1 L, 0-5° C.), and dried in a vacuum oven at 40° C.

Intermediate 4

3-Bromo-pyridine-2-carboxylic acid methyl ester

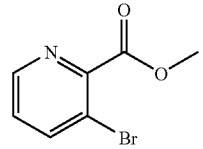

3-Bromo-pyridine-2-carbonitrile (14.7 g, 80 3 mmol) is dissolved in concentrated HCl (50 mL) and heated to 110° C. for 18 h. The mixture is cooled to 0° C., filtered, rinsed with a small amount of ether, and dried in an oven under reduced pressure. The resulting brown solid is dissolved in methanol (80 mL), concentrated $H_2SO_4$ (6.6 mL) is added dropwise, and the solution is heated to 90° C. for 16 h. The methanol is removed under reduced pressure, saturated aqueous sodium bicarbonate is added to obtain a basic pH, and the mixture is extracted with ethyl acetate. The combined extracts are washed with brine, dried over $MgSO_4$, filtered, and concentrated under reduced pressure to yield 12.8 g (74%) of the title compound as a white solid. GCMS m/e 215, 217 $[M]^-$.
Alternate Procedure:
A 50 L three-neck round bottom flask is equipped with a mechanical stirrer, thermocouple, nitrogen inlet and reflux condenser. The flask is charged with HCl (20 L) and 3-bromopyridine-2-carbonitrile (6790 g, 37.1 mol) (prepared, for example, essentially as described in the Alternate Procedure for Intermediate 3). The reaction mixture is heated to reflux and the starting material dissolves and a pink suspension forms. The reaction mixture is stirred for 20 h at reflux. The reaction progress is monitored by TLC (heptane:EtOAc, 1:1). No starting material is present at $R_f$=0.5 or intermediate amide at $R_f$=0.15. Once the reaction is deemed complete, the reaction mixture is cooled to 0-5° C. and then stirred at this temperature for 3 h. After this time the solids are collected by filtration (do not wash and press on a filter). The solids (3-bromopyridine-2-carboxylic acid) are dried in a vacuum oven at 50° C. with use of appropriate trapping as HCl is present in the wet product. A 50 L three-neck round bottom flask is equipped with a mechanical stirrer, thermocouple and reflux condenser. The flask is charged with MeOH (25.5 L), and 3-bromoopyridine-2-carboxylic acid (5.098 kg) followed by HCl (15 mL). The reaction mixture is heated to reflux at about 64-65° C. and stirred at this temperature for 9 h. The reaction mixture is allowed to cool to 40-50° C. and then concentrated to a paste. A 50 L separatory funnel is charged with water (12

L) and solid NaHCO$_3$ (2338 g) and the mixture is stirred for 10-15 min. The residue from the concentrated paste is added in portions to the stirred sodium bicarbonate solution at a rate to control foaming. After all of the residue is added, EtOAc (10 L) is charged to the to the funnel and stirred for 10-15 min. The aqueous layer is separated and the organic layer washed with saturated aqueous sodium bicarbonate solution (1 L), then dried over magnesium sulfate, filtered, and concentrated. The combined aqueous layers are extracted with EtOAc (2×2 L) and the combined organic layers are washed with saturated aqueous sodium bicarbonate solution (1 L), then dried over magnesium sulfate, filtered, and concentrated along with the first extract. A pale yellow oil is obtained which solidifies on cooling. The resulting material is dried in a vacuum oven overnight at room temperature.

Intermediate 5

(3-Bromo-pyridin-2-yl)-methanol

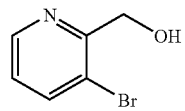

3-Bromo-pyridine-2-carboxylic acid methyl ester (12.8 g, 59 2 mmol) is dissolved in methanol (150 mL) and cooled to 0° C. To the mixture is added NaBH$_4$ (11.2 g, 296 mmol) in 1.0 g portions. The mixture is warmed to room temperature and stirred for 3 h. The methanol is removed under reduced pressure, ethyl acetate is added and the solution is washed with saturated, aqueous ammonium chloride and brine. The organic portion is dried over MgSO$_4$, filtered, and concentrated under reduced pressure to yield 6.8 g (62%) of the title compound as a white solid. GCMS m/e 187, 189 [M]$^-$.

Alternate Procedure:

Two 50 L three-neck round bottom flasks are each equipped with a mechanical stirrer, thermocouple, nitrogen inlet, and drying tube. Each flask is charged with 3-Bromo-pyridine-2-carboxylic acid methyl ester (1886 g, 8.73 mol) (prepared, for example, essentially as described in the Alternate Procedure for Intermediate 4) and MeOH (19 L). The reaction mixture is cooled to −5 to 5° C. using MeOH/dry ice baths, with the dry ice being added in portions while being careful not to overcool. Sodium borohydride (about 1651 g, 43.64 mol) is charged to each flask in 100 g portions, maintaining the temperature at −5 to 5° C. and allowing the temperature to stabilize before adding each portion. After the addition is complete, the MeOH baths are replaced with ice water. The reaction mixture is stirred for 6-8 h at 0-5° C., being careful to maintain the temperature at 0-5° C. with the addition of ice to the baths as necessary. The reaction progress is monitored by TLC (heptane:EtOAc, 1:1). No starting material should be present at R$_f$=0.6 and product is observed at R$_f$=0.1-0.5. Once the reaction is deemed complete, the ice water baths are replaced with ice/MeOH or MeOH/dry ice baths. Acetone is added (4.5 L to each flask) at such a rate to maintain the temperature below 10° C. for the first half of addition and at 10-20° C. for the second part. Once the acetone addition is complete, the reaction may be left to stir overnight in an ice water bath or proceed to work up. Each reaction mixture is diluted with water (5 L to each flask) and the reaction mixture is concentrated to almost dryness. The resulting solid residue is diluted with water (total 15 L) and EtOAc (20 L) and the mixtures are transferred to a 15 gal crock. 50% Sodium hydroxide solution is charged to the mixture (2 kg) and the mixture/suspension is stirred for 20-30 min at room temperature. The mixture is filtered and the filter cake washed with EtOAc (2×2 L), saving the solids. The combined filtrates are combined to a separatory funnel and the organic layers separated, dried over magnesium sulfate, filtered and concentrated. The aqueous layer is saved. The solids from the filtration and the aqueous layer are charged to a 15 gal crock with water (15 L) and EtOAc (15 L). The mixture is stirred for 20-30 min at room temperature. After this time, the mixture is filtered, the organic layer separated and dried over magnesium sulfate, filtered, and concentrated along with the first extract. Extraction is repeated as necessary. The combined concentrated filtrate (3.12 kg of pinkish oil) may be stored in a cold room or may be purified right away. The concentrated filtered residue (3.12 kg) is dissolved in EtOAc (6 L), applying heat as needed. The resulting pinkish solution is diluted with heptane (6 L) and the resulting solution is loaded onto a silica gel plug (5.5 kg, d=24 in, h=2 in, preloaded in a mixture of heptane (9 L) and EtOAc (1 L)) and eluted with heptane:EtOAc, 8:2 mixture (about 30 L) and then heptane:EtOAc, 7:3 mixture (about 40 L). The fractions are monitored by TLC (heptane:EtOAc, 1:1). The product fractions are concentrated to a state of suspension, but not to dryness. The suspension is cooled to 0-5° C. and stirred at this temperature for one hour. After this time, the solids are collected by filtration, washed with heptane (0-5° C., 2 L), and then dried in a vacuum oven at 25° C. to constant weight.

Intermediate 6

3-Bromo-2-(5-chloro-2-iodo-phenoxymethyl)-pyridine

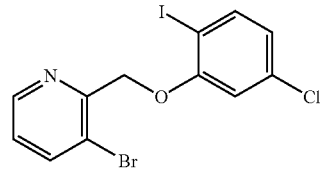

(3-Bromo-pyridin-2-yl)-methanol (3.4 g, 18 mmol), and 2-iodo-5-chlorophenol 4.5 g, 18 mmol), are dissolved in benzene (60 mL) and cooled to 0° C. To the solution is added tributylphosphine (15 mL, 90 mmol), and 1,1'-(azodicarbonyl) dipiperidine (ADDP) (6.6 g, 18 mmol) and the mixture is heated at 40° C. for 3 h. The reaction mixture is diluted with ethyl acetate, washed with saturated aqueous NH$_4$Cl and brine, dried over MgSO$_4$, filtered, and concentrated under reduced pressure. The resulting residue is purified by flash chromatography (Biotage® Si65M, 15% ethyl acetate/hexane) to yield 3.77 g (51%) of the title compound as a white solid. GCMS m/e 296, 298 [M-I]$^-$.

Alternate Alkylation Method:

(3-Bromo-pyridin-2-yl)-methanol (7.39 g, 39.30 mmoles), and triethylamine (7.15 mL, 51.3 mmoles) are combined in tetrahydrofuran (70 mL) under nitrogen. The solution is chilled to 0.6° C. with an ice bath. Methanesulfonyl chloride (3.35 mL, 43.28 mmol) is added dropwise over 20 min, controlling the exotherm such that the internal temperature does not exceed 5° C. Following the addition, the reaction is stirred over an ice bath. After 20 min HPLC analysis shows that the (3-Bromo-pyridin-2-yl)-methanol is fully consumed. Triethylamine hydrochloride is filtered using a fitted glass funnel, washing with cold THF (50 mL). The THF filtrate containing the mesylate is placed under nitrogen and chilled in an ice bath. 2-Iodo-5-chlorophenol (10.00 g, 39.30 mmoles) is added, followed by addition of sodium t-butoxide (4.10 g, 41.38 mmol) in two equal portions with a mild exotherm of about 5° C. for each addition. The ice bath is removed and the reaction allowed to stir overnight. The reaction is quenched with water (50 mL) and the lower aqueous layer allowed to slowly separate. The organic portion is washed with brine (25 mL), and then the brine and aqueous portions back-extracted with THF (10 mL). The organic portions are combined and dried over sodium sulfate, filtered, and concentrated to afford a rusty orange solid. The solid is dissolved in dichloromethane (25 mL) and chromatographed on an AnaLogix Inc., Intelliflash 180 automated chromatography instrument, version 1.8.0. using a gradient of 10- 20% ethyl acetate/hexanes over 35 min to afford 11.0 g (65%) of the product as a yellow solid. $^1$H NMR (DMSO) δ 5.31 (2H, s), 6.85 (1H, dd), 7.25 (1H, m), 7.39 (1H, dd), 7.77 (1H, d), 8.17 (1H, d), 8.59 (1H, d).

Intermediate 7

3-Bromo-2-(2-but-1-ynyl-5-chloro-phenoxymethyl)-pyridine

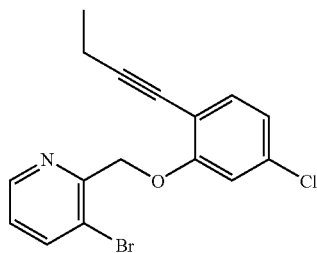

3-Bromo-2-(5-chloro-2-iodo-phenoxymethyl)-pyridine (3.8 g, 8.9 mmol), is placed in a pressure flask, dissolved in diethylamine:acetonitrile:THF (18 mL:4 mL:4 mL), and degassed with nitrogen for 15 min. An excess of 1-butyne is bubbled through the solution followed by the addition of CuI (507 mg, 2.66 mmol), and PdCl$_2$(PPh$_3$)$_2$ (623 mg, 0.888 mmol). The mixture is stirred at room temperature for 1 h. The mixture is then diluted with ether and washed with saturated aqueous ammonium chloride and brine. The organic portion is dried over MgSO$_4$, filtered, and concentrated under reduced pressure. The residue is purified by flash chromatography (Biotage® Si65M, 30% hexane/CH$_2$Cl$_2$ then 20% ethyl acetate/hexane) to provide 2.3 g (75%) of the title compound as a pale orange solid. LCMS m/e 351 [M]$^+$.
Alternate Procedure:
3-Bromo-2-(5-chloro-2-iodo-phenoxymethyl)-pyridine (5.00 g, 11.54 mmoles) is suspended in triethylamine (60 mL, 430.5 mmol) and degassed. 1-Butyne (2.6 g, 11.54 mmol) (24% wt/wt in DMF) is added followed by bis(triphenylphosphine)palladium(II) chloride (410 mg, 0.584 mmol) and copper(I) iodide (220 mg 1.16 mmol). The reaction is allowed to stir overnight. The reaction is diluted with tert-butyl methyl ether (50 mL) and quenched with NH$_4$Cl solution (50 mL), which is accompanied by a slight exotherm of 3° C., and stirred for 30 min. The aqueous layer is removed and the organics washed with 5N HCl (80 mL) to rid the organic layer of TEA. The acidic layer (pH=2) is removed and the organic layer is washed with brine, dried, filtered and evaporated down to a dark brown oil. The oil is chromatographed on AnaLogix Inc., Intelliflash 180 automated chromatography instrument, version 1.8.0. using a gradient from 0% to 10% ethyl acetate in heptane for 5 min, held for 5 min, and a gradient from 10% to 20% ethyl acetate in heptane for 10 min. An orange solid (4.0 g) is obtained which is a mixture of starting material and expected product. The material is recrystallized from heptane to provide 3.1 g of a mixture of starting material (6% by HPLC) and title product. $^1$H NMR (DMSO) δ 1.05 (3H, t), 2.33 (2H, q), 5.31 (2H, s), 6.96 (1H, dd), 7.22 (1H, m), 7.31 (1H, d), 7.37 (1H, dd), 8.15 (1H, dd), 8.57 (1H, dd). The material contains 6% of starting material as determined by HPLC: column—Zorbax Eclipse XDB-C8; solvent—gradient of 50% acetonitrile/water (with 0.01% TFA) to 80% acetonitrile. T$_R$ of product=6.15 min.
Alternate Synthesis:
A. Preparation of 2-(5-Chloro-2-iodo-phenoxy)-tetrahydropyran A 22 L three-neck round bottom flask is equipped with a mechanical stirrer, addition funnel, nitrogen inlet, drying tube and thermocouple placed in a cooling tub. 5-chloro-2-iodophenol (2290 g, 9 mol) (prepared, for example, essentially as described in the Alternate Procedure for Intermediate 1), dichloromethane (11.45 L) and pyridinium p-toluene-sulfonate (45.2 g, 0.18 mol) are charged to the flask and 3,4-dihydro-2H-pyran (1211 g, 14.4 mol) is added dropwise over approximately one hour to the flask. A mild exotherm is observed during the addition, and cold tap water is added to the cooling bath to maintain the temperature ≦30° C. After the addition is complete, the reaction mixture is stirred for a minimum of 12 h at ambient temperature. The reaction progress is monitored by TLC (heptane:EtOAc, 9:1). The starting material is observed at Rf=0.2 and product at R$_f$=0.5. If more than traces of starting material are present then the reaction may be stirred for an additional 4 h. Once the reaction is complete, the mixture is washed with a saturated aqueous sodium bicarbonate solution (1.5 L), the organic layer separated from the aqueous layer, the aqueous layer extracted with dichloromethane (1 L), and the combined organic layers are dried over sodium sulfate, treated with charcoal, filtered, and concentrated. The resulting brown oil is co-evaporated with toluene to remove possible residual 3,4-dihydro-2H-pyran. The product is dissolved in triethylamine (4.5 L) to form a hazy solution, filtered, and the filter cake washed with triethylamine (200 mL). The product is subsequently used as a solution in triethylamine in the next reaction.
B. Preparation of 2-(2-But-1-ynyl-5-chloro-phenoxy)-tetrahydro-pyran The product in triethylamine solution from the previous reaction above is charged to a 50 L three neck round bottom flask equipped with a mechanical stirrer, nitrogen inlet, drying tube, and thermocouple placed in a cooling tub. Triethylamine (4.28 L), ethyl acetate (8.78 L), dichlorobis(triphenylphosphine) palladium (126.3 g, 0.18 mol), and copper (I) iodide (34.3 g, 0.18 mol) are charged to the flask and the reaction mixture is stirred and cooled to 0-10° C. under a nitrogen blanket (Note: the product may also be initially dissolved in 9 L of triethylamine in Part A without the subsequent addition of additional triethylamine as described above). After this time, the nitrogen flow is discontinued and 1-butyne (681.5 g, 12.6 mol) is charged to the flask using a glass dip tub placed below the reaction mixture surface, maintaining the temperature ≦10° C. during the three hour addition. After the addition is complete, the cooling bath is removed and the reaction mixture stirred for a minimum of 12 h at room temperature. The reaction is monitored by TLC (heptane:EtOAc, 9:1). Starting material is observed at R$_f$=0.6 and product at $R_f$=0.5. Once the reaction is deemed complete, the reaction mixture is filtered, the filter cake washed with EtOAc (3×1 L), releasing the vacuum for each wash. All the organic portions are combined and concentrated to a brown oil. The residue is diluted with heptane (5 L) and triethylamine (25 mL). The product is purified using a silica gel column (3 kg of silica gel preloaded in heptane (5 L) and triethylamine (60 mL), d=8 in, h=18 in). The crude product is loaded in solution, and eluted sequentially with heptane (9 L)/0.2% EtOAc, heptane (9 L)/3% EtOAc, and heptane (9 L)/4% EtOAc. The appropriate fractions are combined to provide a brown oil (2644 g, not clean). The oil is dissolved in heptane (1 mL/g) and triethylamine (20 mL) and the solution is placed in a freezer. Solids separate after about 12 h. The supernatant is decanted, the solids weighed and dissolved in heptane (1 mL/g) and triethylamine (20 mL). The crystallization is repeated to obtain pure product (2003 g).

Additional Purification:

The solids are dissolved in dichloromethane (2 mL/g) and the resulting solution is charged to an appropriate three neck round bottom flask equipped with a mechanical stirrer, nitrogen inlet, and drying tube placed in a cooling tub. Si-thiol derivatized silica gel (loading 1.33 mmol/g) is added and the resulting suspension is stirred for a minimum of 12 h at room temperature. After this time, the suspension is filtered, the filter cake washed with dichloromethane (3×500 mL) and the combined filtrates concentrated to yield an amber oil. The oil is dissolved in heptane (1 mL/g) and placed in a freezer overnight. The solids are decanted then dried in a vacuum oven at ambient temperature, 1 mm Hg for a minimum of 18 h.

C. Preparation of 2-But-1-ynyl-5-chloro-phenol

A 22 L three neck round bottom flask is equipped with a mechanical stirrer, addition funnel, nitrogen inlet, thermocouple and drying tube placed in a cooling tub. MeOH (2.3 L) and HCl (9 mL) are charged to the flask, stirring is initiated, and the reaction cooled to 10-20° C. A 20 L wide mouth round bottom flask is equipped with a mechanical stirrer placed in a heating mantle and 2-(2-but-1-ynyl-5-chloro-phenoxy)-tetrahydro-pyran (2313 g, 8.736 mol) and MeOH (3.47 L) are charged to the flask. Gentle heating is applied to dissolve the solids and the flask is rinsed with MeOH (70 mL). This solution is charged to the three neck round bottom flask through an addition funnel maintaining the temperature 20° C. over 45 min. Cooling is discontinued and the reaction mixture is stirred for a minimum of 30 min. The reaction progress is monitored by TLC (heptane:EtOAc, 9:1). Starting material is observed at $R_f$=0.6 and product at $R_f$=0.5. Once the reaction is deemed complete, the reaction mixture is diluted with a saturated aqueous sodium bicarbonate solution (300 mL) and stirred for 5-10 min at room temperature. After this time the reaction mixture is concentrated to remove the MeOH. The residual oil (2118 g) is diluted with MTBE (4 L) and washed with a brine solution (1.5 L). The organic layer is separated and the aqueous layer extracted with MTBE (2×1 L). The combined organic portions are dried over magnesium sulfate, filtered, and concentrated. The product is then co-evaporated with toluene (2×800 mL) and used directly as is.

D. Preparation of 3-bromo-2-(2-but-1-ynyl-5-chloro-phenoxymethyl)-pyridine (Intermediate 7)

A 50 L three neck round bottom flask is equipped with a mechanical stirrer, addition funnel, nitrogen inlet, thermocouple, and drying tube placed in a cooling tub. (3-Bromo-pyridin-2-yl)-methanol (prepared, for example, essentially as described in the Alternate Procedure for Intermediate 5) (1837 g, 9.769 mol), THF (14.7 L) and triethylamine (1.53 L, 11.01 mol) are charged to the flask and the reaction mixture cooled to −5 to 5° C. Neat methanesulfonyl chloride (1155 g, 10.09) is added dropwise over 1.5 h maintaining the temperature <5° C. to form a white suspension. The resulting suspension is stirred for one hour at −5 to 0° C. and the reaction progress monitored by TLC (dichloromethane:MeOH, 20:1). Starting material is observed at $R_f$=0.5 and mesylate product $R_f$=0.95. Once the reaction is deemed complete, the reaction mixture is filtered and the filter cake washed with cold THF (0-5° C., 3×2 L).

A 50 L three neck round bottom flask is equipped with a mechanical stirrer, addition funnel, nitrogen inlet, thermocouple, and drying tube placed in a cooling tub. The combined filtrates containing methanesulfonic acid 3-bromo-pyridin-2-ylmethyl ester and 2-but-1-ynyl-5-chloro-phenol (8.736 mol, 0.95 eq) (prepared, for example, essentially as described in Step C, above) are charged to the flask, using THF (70 mL) to rinse the flask. Stirring is initiated and the reaction mixture cooled to −15 to 0° C. Sodium tert-butoxide (969.7 g, 10.09 mol) is added in portions over 40 min keeping the temperature <0° C. The reaction is allowed to warm to room temperature with stirring for a minimum of 48 h until a hazy tan/yellow solution is present. The reaction progress is monitored by TLC (heptane:EtOAc, 1:1). The mesylate is observed at $R_f$=0.1 and product $R_f$=0.5. Once the reaction is deemed complete, the reaction mixture is diluted with water (5 L), the organic layer is separated from the aqueous layer, and the organic concentrated to a thick slurry. The aqueous layer is extracted with MTBE (2×2 L) and the organic layer separated. The concentrated slurry is dissolved in MTBE (12 L), combined with the previous extractions (4 L) and stirred until all the solids are dissolved. The organic layer is washed with brine (3 L), separated, dried over magnesium sulfate, treated with charcoal, filtered, and concentrated. The product is then co-evaporated with EtOH (1 L), resulting in off-white solids (3581 g). The solids are recrystallized from EtOH (2.5 L, 0 7 mL/g), with stirring and cooling at −5 to 5° C. for one hour. The solids are collected by filtration and washed with cold EtOH (2×900 mL, −20 to −10° C.). The product is dried in a vacuum oven at 30° C. using an oil pump.

Intermediate 8

(Z)-2-{2-[1,2-Bis-(4,4,5,5-tetramethyl-[1,3,2]dioxaborolan-2-yl)-but-1-enyl]-5-chloro-phenoxymethyl}-3-bromo-pyridine

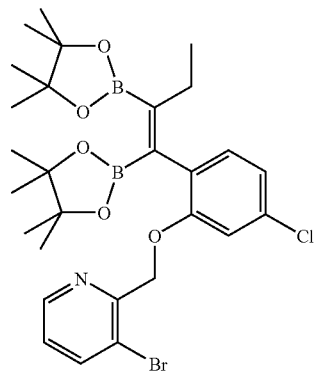

3-Bromo-2-(2-but-1-ynyl-5-chloro-phenoxymethyl)-pyridine (2.3 g, 6.6 mmol), is dissolved in DMF (65 mL) and degassed by bubbling nitrogen through the solution for 15 min. To the solution is added bis(pinocalato)diboron (1.8 g, 7.2 mmol), and Pt(PPh$_3$)$_4$ (653 mg, 0.525 mmol). The mixture is heated at 80° C. for 24 h, cooled to room temperature, diluted with ethyl acetate, washed with brine, dried over MgSO$_4$, filtered, and concentrated under reduced pressure to give a solid. The solid is dissolved in ether, filtered, and concentrated under reduced pressure to give 3.61 g (91%) of the title compound as a yellow solid which is used without further purification. LCMS m/e 605 [M]$^+$.

Alternate Procedure:

A 50 L three neck round bottom flask is equipped with a mechanical stirrer, nitrogen dip tube, thermocouple, and drying tube placed in a cooling tub. DMF (27 L), 3-bromo-2-(2-but-1-ynyl-5-chloro-phenoxymethyl)-pyridine (3381 g, 9.642 mol) (prepared, for example, essentially as described in the Alternate Synthesis for Intermediate 7) is charged to the flask and the resulting solution is stirred at room temperature while bubbling a strong nitrogen gas flow for a minimum of one hour. After this time bis(pinacolatodiboron) (2522 g, 9.93 mol) is charged in one portion to the flask and the resulting solution is stirred at room temperature while bubbling a strong nitrogen gas flow for at least 15 min. Tetrakis(triphenylphoshine) platinum (0) (24 g, 0.019 mmol) is charged to the flask and the dip tube is replaced with normal nitrogen inlet. The reaction mixture is heated to 80° C. and stirred at this temperature for 8-10 h. The reaction progress is monitored by TLC (heptane:EtOAc). No starting material should be present at R$_f$=0.4 and product is observed at R$_f$=0.35. Once the reaction is deemed complete, the reaction mixture is cooled to room temperature. The reaction mixture is diluted with MTBE (20 L) followed by a 10% aqueous NaCl solution (25 L). The organic layer is separated from the aqueous layer and washed with a 10% aqueous NaCl solution (10 L). The organic layer is separated and dried over magnesium sulfate, filtered, and concentrated. The aqueous layers are combined and extracted with MTBE (5 L). The MTBE extracts are washed with a 10% aqueous NaCl solution (3 L), dried with magnesium sulfate, filtered, and concentrated along with the first extract to a thick paste. Isopropyl alcohol (7 L) is added and concentration is continued to remove the residual MTBE. The resulting suspension is stirred in a cooling bath for a minimum of one hour at room temperature. After this time the solids are collected by filtration and the filter cake washed with isopropyl alcohol (2×1.5 L). The solids are dried in a vacuum oven at 40-45° C. for a minimum of 18 h using an oil pump.

Intermediate 9

(Z)-8-Chloro-5-[1-(4,4,5,5-tetramethyl-[1,3,2]dioxaborolan-2-yl)-propylidene]-5,11-dihydro-10-oxa-1-aza-dibenzo[a,d]cycloheptane

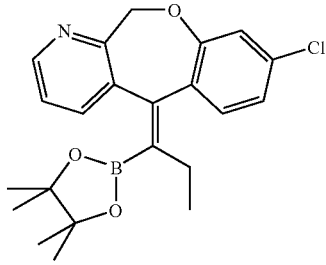

(Z)-2-{2-[1,2-Bis-(4,4,5,5-tetramethyl-[1,3,2]dioxaborolan-2-yl)-but-1-enyl]-5-chloro-phenoxymethyl}-3-bromo-pyridine (3.6 g, 6 0 mmol) is dissolved in dioxane (600 mL) and degassed by bubbling nitrogen through the solution for 15 min. Crushed K$_3$PO$_4$ (3.8 g, 18 mmol) is added followed by PdCl$_2$dppf.CH$_2$Cl$_2$ (488 mg, 0.598 mmol). The slurry is heated at 80° C. for 22 h, cooled to room temperature, washed with brine, dried over MgSO$_4$, and concentrated under reduced pressure to give a solid. The solid is dissolved in ethyl acetate, gravity filtered, and concentrated under reduced pressure to give 2.37 g (about 100%) of the title compound which is used without further purification. LCMS m/e 398 [M+H]$^+$.

Alternate Synthesis:

Two 50 L three neck round bottom flasks are equipped with a mechanical stirrer, nitrogen dip tube, thermocouple, reflux condenser and drying tube placed in heating mantles. 1,4-Dioxane (26 L in each), (Z)-2-{2-[1,2-bis-(4,4,5,5-tetramethyl-[1,3,2]dioxaborolan-2-yl)-but-1-enyl]-5-chloro-phenoxymethyl}-3-bromo-pyridine (prepared, for example, essentially as described in the Alternate Procedure of Intermediate 8) (2610 g in each) and potassium carbonate powder (1790 g in each) are charged to the flasks. The resulting suspension is stirred at room temperature while bubbling in a strong nitrogen gas flow for at least 2 h. After this time [1,1'-bis(diphenylphosphino)-ferrocene]dichloropalladium (II), complex with dichloromethane (1:1), (176.3 g in each) is charged to the flasks and the dip tube is replaced with a normal nitrogen inlet. The reaction mixture is heated to 80° C. and stirred at this temperature for a minimum of 20 h. A dark brown suspension is observed. The reaction progress is monitored by TLC (heptane:EtOAc 1:1) Traces of starting material are present at R$_f$=0.7 and product is observed at R$_f$=0.6. If more than traces of starting material are present then additional potassium carbonate (596.5 g in each, total 1193 g) is added. The reaction mixtures are stirred for 4 h at 80° C. Once the reactions are deemed complete, the reaction mixtures are cooled to 60° C. or stirred to room temperature. The reaction mixtures are filtered and the filter cakes washed with 1,4-dioxane (3×3 L) and EtOAc (3×3 L). The combined filtrates are concentrated to solids. The dark solids are dissolved in EtOAc (20 L), and the resulting solution is washed with a 15% aqueous NaCl solution (5 L). The mixture is agitated (using a separatory funnel). No separation occurs. The mixture is collected in pails and diatomaceous earth is added (1 kg to each pail), the pails are agitated and the whole mixture is filtered to remove solids that obstruct the layer separation. The filter cake is washed with EtOAc (3×1 L). The filtrates are combined and the organic layer is separated. The organic layer is washed with a 15% aqueous NaCl solution (5 L). The organic layers are then combined, dried over magnesium sulfate, filtered, and concentrated. Co-evaporate with 1,4-dioxane (2 L) to obtain a brownish solids residue.

Example 1

(E)-N-{3-[1-(8-Chloro-11H-10-oxa-1-aza-dibenzo[a,d]cyclohepten-5-ylidene)-propyl]-phenyl}-methanesulfonamide

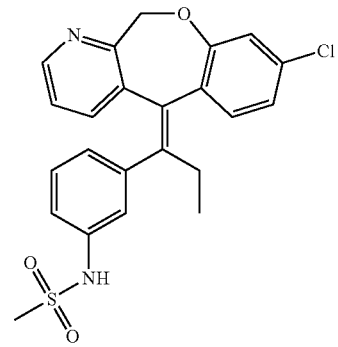

(Z)-8-Chloro-5-[1-(4,4,5,5-tetramethyl-[1,3,2]dioxaborolan-2-yl)-propylidene]-5,11-dihydro-10-oxa-1-aza-dibenzo

[a,d]cycloheptane (2.37 g, 5.96 mmol), N-(3-iodophenyl)methanesulfonamide (2.66 g, 8.94 mmol), 3,5-dimethoxyphenol (4.6 g, 30 mmol), and KOH (5.0 g, 89 mmol) are dissolved in dioxane/water (40 mL/15 mL) and degassed by bubbling nitrogen through the solution for 15 min. To the mixture is added Pd(PPh₃)₄ (689 mg, 0.596 mmol), and the solution is heated at 80° C. for 18 h. The solution is cooled to room temperature, diluted with ethyl acetate, washed with water, saturated aqueous ammonium chloride, and brine, dried over MgSO₄, filtered, and concentrated under reduced pressure. The resulting residue is purified by flash chromatography (Biotage® Si65M, 3% ethanol/CHCl₃) followed by ion exchange chromatography (split into two portions, BondElut® SCX, flush with 80/20 CH₂Cl₂/methanol, elute with 80/20 CH₂Cl₂/2.0M NH₃ in methanol), and another flash chromatography purification (Biotage® Si40M, 40% ethyl acetate/hexane to 80% ethyl acetate hexane) to yield 1.01 g (38%) of the title compound as a white solid. LCMS m/e 441 [M+H]⁺.

Intermediate 10

(E)-3-[1-(8-Chloro-11H-10-oxa-1-aza-dibenzo[a,d]cyclohepten-5-ylidene)-propyl]-phenylamine

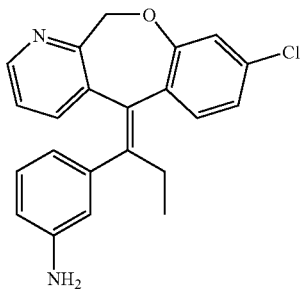

Under a nitrogen atmosphere, a solution of potassium hydroxide (500 g, 8.91 moles) in water (1.50 L) is charged to a 12 L 4 neck round bottom flask equipped with a mechanical stirrer, reflux condenser, and thermocouple. To the solution is added 3-iodoaniline (128 g, 585 mmoles), (Z)-8-chloro-5-[1-(4,4,5,5-tetramethyl-[1,3,2]dioxaborolan-2-yl)-propylidene]-5,11-dihydro-10-oxa-1-aza-dibenzo[a,d]cycloheptane (232 g, 583 mmoles), 1,4-dioxane (2.40 L), and 3,5-dimethoxyphenol (454 g, 2.92 moles) resulting in the formation of a dark brown mixture. The mixture is degassed through a three-way valve placed on the reflux condenser. House vacuum is applied through the three way valve for approximately 3 min. A nitrogen purge is then applied to the evacuated flask. This is repeated for a total of three times. Solid tetrakis(triphenylphosphine)palladium (20.4 g, 17.5 mmoles) is added and the degassing procedure is repeated. The dark brown mixture is heated to 80° C. for 2 h. The reaction mixture is cooled to 40° C. and charged to a 22 L bottom outlet flask that contains 15% NaCl solution (2.5 L). The mixture is stirred for 10 min and the layers separated. The organic layer is washed with 15% NaCl solution (2.5 L) a second time. The organic layer is isolated and concentrated in vacuo yielding a thick dark oil. Two liters of heptane are added and concentrated in vacuo to remove residual dioxane. The product is purified by large scale silica gel chromatography using a 10 in. (about 25 cm) sintered glass funnel packed with 3 kg of silica-gel wet with heptane. The material is dissolved in heptane (approximately 500 mL) and applied to the silica. Using slight vacuum, the material is charged on to the silica with 3 L of heptane as the eluent. The mobile phase is changed to 9:1 heptane:EtOAc and a gradient to 1:1 heptane:EtOAc is used while collecting 3.5 L fractions. The fractions are monitored using TLC (1:1 EtOAc:heptane, SiO₂, R_f=0.45). The fractions containing desired product are combined and concentrated in vacuo yielding a dark green oil. To the oil is added heptane (2 L) and then the material concentrated in vacuo to provide 201.3 g (95%) of a dark green solid. LC-ES/MS m/e 363.2 [M+H]⁺.

Alternate Procedure:

(E)-3-[1-(8-Chloro-11H-10-oxa-1-aza-dibenzo[a,d]cyclohepten-5-ylidene)-propyl]-phenylamine, ditoluenesulfonic acid salt (5765 g) (prepared, for example, essentially as described for Intermediate 11 below using the Alternate Synthesis), is suspended in water (12 L) and EtOAc (12 L) using a 40 L separatory funnel A 50% NaOH solution (4.8 kg,) is added in one portion. The suspension is agitated until all of the solids dissolve. The organic layer is separated and washed with a 5% aqueous NaOH solution (1 L). The combined aqueous layers are extracted with EtOAc (2×2 L). The organic layer is separated and washed with a 5% aqueous NaOH solution (500 mL). The combined organic layers are dried over magnesium sulfate, treated with charcoal, and filtered. The filtrate is diluted with heptane (16 L) making a solution of heptane:EtOAc, 1:1). The product is purified using a silica gel plug (6 kg of silica gel preloaded in heptane:EtOAc, 1:1, (8 L), diameter=18 in, height=3 in). The crude product is loaded in solution, and eluted with heptane:EtOAc, 1:1, (about 40-50 L), then heptane:EtOAc, 1:3, (about 20-30 L) and then heptane:EtOAc, 1:9, (10-20 L). The fractions containing product are determined by TLC (EtOAc, 100%). The impurity is observed at R_f=0.0. The product is observed at R_f=0.4. The fractions containing product are combined and concentrated to form a paste. The resulting residue is diluted with heptane (2-3 L). The suspension is stirred for 30 min at room temperature and the solids collected by filtration, washing with heptane (2×1.5 L). The solids are dried in a vacuum oven at 40-45° C. overnight.

Example 1(a)

From Intermediate 10

(E)-N-{3-[1-(8-Chloro-11H-10-oxa-1-aza-dibenzo[a,d]cyclohepten-5-ylidene)-propyl]-phenyl}-methanesulfonamide

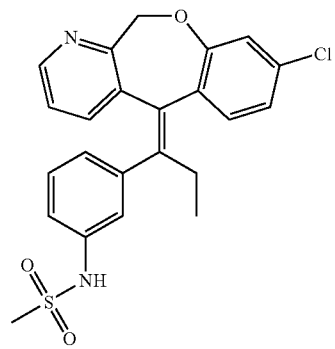

Under a nitrogen atmosphere, solid (E)-3-[1-(8-chloro-11H-10-oxa-1-aza-dibenzo[a,d]cyclohepten-5-ylidene)-propyl]-phenylamine (198 g, 545 mmol), pyridine (67.0 mL, 828 mmol) and dichloromethane (1.6 L) are charged to a 5 liter 4 neck round bottom flask equipped with a mechanical stirrer and thermocouple. To the dark green reaction mixture, a solution of methanesulfonyl chloride (51.0 mL, 658 mmol) in dichloromethane (400 mL) is added dropwise over 20 min from an addition funnel. An exotherm of 6.9° C. is observed over the course of the addition. Upon completion of addition the reaction is stirred for 16 h at ambient temperature. The mixture is charged to a 22 L bottom outlet flask containing 10% citric acid solution (2 L). The mixture is stirred for 15 min and the layers separated upon standing. The organic layer is washed with a 15% NaCl solution. The organic layer is charged to a 5 L 4 neck flask, equipped with a mechanical stirrer under a nitrogen atmosphere. The deep red solution is treated with DARCO® activated charcoal (200 g), $Na_2SO_4$ (200 g) and TMT (trithiocyanuric acid trisodium salt hydrate) (50 g). The mixture is stirred for 18 h at ambient temperature and then filtered over a 2 in (about 5 cm) pad of diatomaceous earth (Hy-flo Supercel®). The filtrate is concentrated in vacuo yielding a hard white foam. Isopropyl alcohol (1 L, 5 volumes) is added to the foam and the slurry is stirred at 40° C. for one hour. The thick mixture is cooled to ambient temperature. The solids are vacuum filtered over a polypropylene pad in a buchner funnel The material is dried at 70° C. for 16 h under house vacuum yielding 171.85 g (71.4%) of white crystalline product. LC-ES/MS m/e 441.2 $[M+H]^+$, 439.1 $[M-H]^-$. Anal. Calcd for $C_{23}H_{21}N_2ClO_3S$: C, 62.65; H, 4.80; N, 6.35. Found: C, 62.81; H, 4.82; N, 6.20.

Intermediate 11

(E)-3-[1-(8-Chloro-11H-10-oxa-1-aza-dibenzo[a,d] cyclohepten-5-ylidene)-propyl]-phenylamine, ditoluenesulfonic acid salt

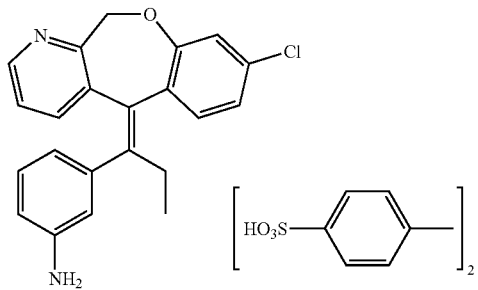

The titled compound is prepared essentially as described for Intermediate 10 using 3-iodoaniline (13.72 g, 62.64 mmol) and (Z)-8-chloro-5-[1-(4,4,5,5-tetramethyl-[1,3,2]dioxaborolan-2-yl)-propylidene]5,11-dihydro-10-oxa-1-aza-dibenzo[a,d]cycloheptane (24.91 g, 62.64 mmol). After the reaction is complete it is cooled to 40° C. Water (250 mL), 15% brine solution (50 mL) and t-butyl methyl ether (250 mL) are added. The top organic layer is separated and the aqueous layer is extracted with t-butyl methyl ether (100 mL). The organic solution is passed over a silica pad in a prepacked 70 mm SUPELCO® Buchner Funnel The filtrate is concentrated to provide 42.45 g of an oil. To the oil is added EtOAc (200 mL) followed by toluenesulfonic acid monohydrate (23.83 g) with stirring for 18 h. Filter the tan precipitate and wash with EtOAc (100 mL) followed by heptane (50 mL) and 1:1 EtOAc/heptane (50 mL). The material is dried under house vacuum at 50° C. for 18 h to provide 34.43 g (77.7% wt. yield). LC-ES/MS m/e 362 [M+]; $^1$H NMR DMSO (δ) 0.8 (triplet, 3H), 2.22 (s, 6H), 2.6 (m, 1H), 2.65 (m, 1H), 5.1 (d, 1H), 5.88 (d, 1H), 7-7.5 (Ar and $NH_3$, 21H), 8.2 (d, 1H).
Alternate Synthesis:

Two 50 L three neck round bottom flasks are equipped with a mechanical stirrer, nitrogen inlet, thermocouple, reflux condenser and drying tube placed in cooling tubs. Water (8.5 L in each flask) and potassium hydroxide (2422 g in each flask) are charged to the flasks and the mixtures are stirred for 5-15 min to let the solids dissolve and the temperature stabilize (approximately 40° C.). The mixtures are cooled to 20-30° C. under a nitrogen blanket. After this time, the flasks are placed in heating mantles and 1,4-dioxane (3 L in each flask), 3-iodoaniline (945.5 g, 4.317 mol in each flask), and an evenly divided solution of (Z)-8-chloro-5-[1-(4,4,5,5-tetramethyl-[1,3,2]dioxaborolan-2-yl)-propylidene]-5,11-dihydro-10-oxa-1-aza-dibenzo[a,d]cycloheptane (considered 8.634 mol, 1 eq) (prepared essentially as described in the Alternate Synthesis of Intermediate 9) in 1,4-dioxane (15 L, 7.5 L to each flask) are charged to each flask, followed by 3,5-dimethoxyphenol (3328 g, 21.585 mol in each flask) and tetrakis(triphenylphosphine)palladium (0) (149.58 g, 0.26 mol in each flask). The reaction mixtures are heated to 80° C. and stirred at this temperature for 2 h. A dark solution is observed. The reaction progress is monitored by TLC heptane:EtOAc, 1:1. No starting material should be present at $R_f$=0.6. Product is observed at $R_f$=0.2. Once the reactions are deemed complete, the reaction mixtures are allowed to cool to room temperature. The reaction mixtures are diluted with water and MTBE (8 L). The organic layer is separated and the aqueous layer is extracted with MTBE (4×2 L). The combined organic layers are washed with a brine solution (5 L), dried over magnesium sulfate, treated with charcoal, filtered, and concentrated. Coevaporate with EtOAc (1.5 L) to obtain a light brown oil (4080 g).

A 50 L three neck round bottom flask is equipped with a mechanical stirrer, nitrogen inlet and drying tube placed in a cooling tub. p-Toluenesulfonic acid monohydrate (4106 g, 21.585 mol, 2.5 eq) and EtOAc (15 L) are charged to the flask, stirring is initiated, and a white suspension is observed. The brown oil is dissolved in EtOAc (16.3 L, 4 mL/g) and this solution is added portionwise (fast at first then slow when solids appear) to the suspension of p-toluenesulfonic acid monohydrate in EtOAc. The resulting gray-brown suspension is stirred for 12 h at room temperature. After this time the solids are collected by filtration and washed with EtOAc (3×2 L, room temperature). The solids are transferred to a pail and slurried with EtOAc (14 L) then the solids are collected by filtration. The solids are transferred to a pail and slurried once again with isopropyl alcohol (14 L) then collected by filtration. A 50 L three neck round bottom flask is equipped with a mechanical stirrer, reflux condenser, nitrogen inlet and drying tube placed in a heating mantle. The solids and isopropyl alcohol (12 L) are charged to the flask. The resulting suspension is heated to reflux for 30 min, cooled to room temperature and the solids collected by filtration. The solids are then washed with room temperature isopropyl alcohol (2×2 L), EtOAc (2×2 L), and heptane (2×2 L) and then dried in a vacuum oven at 40 to 45° C. overnight. Gray-brown solids are obtained.

Example 1(b)

(E)-N-{3-[1-(8-Chloro-11H-10-oxa-1-aza-dibenzo[a,d]cyclohepten-5-ylidene)-propyl]-phenyl}-methanesulfonamide A 50 L three neck round bottom flask is equipped with a mechanical stirrer, nitrogen inlet, thermocouple and drying tube placed in a cooling tub. (E)-3-[1-(8-chloro-11H-10-oxa-1-aza-dibenzo[a,d]cyclohepten-5-ylidene)-propyl]-phenylamine (1800 g, 4.96 mol) (prepared essentially as described for Intermediate 10 using the Alternate Procedure) dichloromethane (18 L) and pyridine (588.5 g, 7.44 mol) are added to the flask. The reaction mixture is cooled to 0 to 5° C. and neat methanesulfonyl chloride (681.8 g, 5.952 mol) is added dropwise over about 20-30 min, maintaining the temperature ≦5° C. After the addition is complete, the reaction mixture is stirred at 0 to 5° C. for one hour. The cooling bath is removed and the reaction stirred at room temperature for a minimum of 12 h. The progress of the reaction is followed by TLC (straight EtOAc). Once the reaction is deemed complete, the reaction mixture is washed with a 10% aqueous citric acid solution (14 L) using a 40 L separatory funnel. The aqueous layer is back extracted with dichloromethane (1.5 L). The combined organic layers are washed with a 10% aqueous citric acid solution (2 L). The aqueous layer is back extracted with dichloromethane (1.5 L). The combined organic layers are washed with a 15% aqueous sodium chloride solution (5 L) and the aqueous layer back extracted with dichloromethane (1.5 L). The combined organic layers are washed with a half saturated aqueous sodium bicarbonate solution (5 L). The sodium bicarbonate wash should be performed for a minimum of 30 min. The aqueous layer is back extracted with dichloromethane (1.5 L). The combined organic layers are dried over sodium sulfate and filtered. A 50 L three neck round bottom flask is equipped with a mechanical stirrer, nitrogen inlet, thermocouple and drying tube placed in a cooling tub. The dichloromethane solution containing the product is charged to the flask, followed by trithiocyanuric acid, trisodium salt (630 g, 0.35 g/g of starting material), sodium sulfate (3.6 kg, 2 g/g of starting material) and charcoal (180 g, 0.1 g/g of starting material) to the flask. The suspension is stirred for 12 h at room temperature. The suspension is filtered and the filter cake slurried with dichloromethane (3×3 L). The filtrates are combined and concentrated to an off white solid. The product is dried in a vacuum oven at 40° C. overnight.

Example 1(c)

From Intermediate 11

(E)-N-{3-[1-(8-Chloro-11H-10-oxa-1-aza-dibenzo[a,d]cyclohepten-5-ylidene)-propyl]-phenyl}-methanesulfonamide Part A.
A 250 mL RB flask equipped with a magnetic stirrer is charged with Intermediate 11 (3.14 g, 5.09 mmol) and methylene chloride (70 mL). To the mixture is added 15% sodium carbonate solution in portions over a period of 5 min. The mixture is stirred for 30 min. The lower organic layer is separated and dried with anhydrous $MgSO_4$. The mixture is filtered and the cake washed with methylene chloride (10 mL). The filtrate is concentrated on a rotary evaporator at a bath temperature of 50° C. to obtain 1.85 g of an oil.
Part B.
In a separate 250 mL, 3-necked reaction vessel is added a solution of the oil (1.85 g) from Part A dissolved in methylene chloride (65 mL), and pyridine (0.62 mL, 7.64 mmol). The reaction solution is then stirred for 5 min. Methanesulfonyl chloride (0.46 mL, 6.12 mmol) dissolved in methylene chloride (5 mL) is added over a period of 5 min. The reaction mixture is stirred for 18 h at room temperature. The reaction is monitored by HPLC and quenched with 10% citric acid solution (10 mL) after disappearance of Intermediate 11. The reaction mixture is stirred for 5 min. Deionized water (20 mL) is added and the lower organic layer separated after 20 min of stirring. The organic layer is treated with DARCO® activated charcoal (2.0 g) for 20 min. The mixture is filtered over diatomaceous earth and the cake washed with methylene chloride (20 mL). The filtrate is concentrated on a rotary evaporator to afford 1.84 g of the title compound. LC-ES/MS m/e 440 [M+]; $^1$H NMR DMSO (δ6) 0.8 (triplet, 3H), 2.45 (m, 1H), 2.55 (m, 4H), 5.0 (d, 1H), 5.85 (d, 1H), 6.9-7.1 (m, 7H), 7.2 (d, 1H), 7.38 (d, 1H), 8.24 (d, 1H), 9.45 (s, 1H).

Example 2

(E)-N-{3-[1-(8-Chloro-11H-10-oxa-1-aza-dibenzo[a,d]cyclohepten-5-ylidene)-propyl]-phenyl}-methanesulfonamide $H_2SO_4$ (2:1)

(E)-N-{3-[1-(8-chloro-11H-10-oxa-1-aza-dibenzo[a,d]cyclohepten-5-ylidene)-propyl]-phenyl}-methanesulfonamide (251 mg, 0.57 mmol) is combined with acetone (4 mL) in a scintillation vial. The sample is heated to approximately 55° C. with stirring. A 1 molar equivalence of sulfuric acid (0.25M) is added. After a few hours of elevated heating and stirring, the sample is allowed to cool to approximately 25° C. with stirring overnight. No precipitation occurs and the sample is evaporated to dryness under a nitrogen stream. To the resulting residue, acetone (2 mL) is added, while stirring and heating at approximately 55° C. to provide a suspension. Additional acetone (1 mL) is added resulting in a clear solution. The sample is evaporated to dryness under a nitrogen steam. Acetone (2 mL) is added to the resulting residue, while stirring and heating at approximately 55° C. to provide a suspension. The sample is allowed to cool to approximately 25° C. with stirring overnight. The suspension is isolated by vacuum filtration and the solid is allowed to air dry. The melting point characteristics of the material are determined by differential thermal analysis (DTA). Onset melt=139° C.; Peak melt=148° C. The material is determined to be the hemisulfate salt by HPLC (Waters 2695 (Alliance) model auto injector, Chromolith Performance RP-18 column eluting with 5% acetonitrile/water (with 0.1% TFA) to 100% acetonitrile (with 0.1% TFA) at 1 mL/min) with an ESA Corona™ detector to quantify the counterion and found to contain 56.7% of the theoretical mono-salt. The free base is detected by UV (245 nm, PDA Waters 996 detector) and found to be at 89.5% potency in comparison to a standard curve. This corresponds to a stoichiometry of 2 moles of free base: 1 mole of $H_2SO_4$ (hemisulfate salt).

Example 3

(E)-N-{3-[1-(8-Chloro-11H-10-oxa-1-aza-dibenzo[a,d]cyclohepten-5-ylidene)-propyl]-phenyl}-methanesulfonamide HBr (E)-N-{3-[1-(8-chloro-11H-10-oxa-1-aza-dibenzo[a,d]cyclohepten-5-ylidene)-propyl]-phenyl}-methanesulfonamide (183 mg, 0.42 mmol) is combined with ethanol (5 mL) in a scintillation vial. The sample is heated to approximately 75° C. with stirring. A 1 molar equivalence of HBr (0.25M) is added. After a few hours of elevated heating and stirring, the sample is allowed to cool to approximately 25° C. with stirring overnight. No precipitation occurs and the sample is evaporated to dryness under a nitrogen stream. To the resulting residue is added "wet" EtOAc (6 mL) which is prepared by washing the EtOAc with water in a separatory funnel to give approximately 3% water/EtOAc. The resulting suspension is stirred and heated at approximately 65° C. for several hours. The sample is allowed to cool to approximately 25° C. with stirring overnight. The solid is isolated from the suspension by vacuum filtration and allowed to air dry. The melting point characteristics of the material are determined by differential thermal analysis (DTA). Onset melt=227° C.; Peak melt=233° C.

Example 4

(E)-N-{3-[1-(8-Chloro-11H-10-oxa-1-aza-dibenzo[a,d]cyclohepten-5-ylidene)-propyl]-phenyl}-methanesulfonamide HCl (E)-N-{3-[1-(8-chloro-11H-10-oxa-1-aza-dibenzo[a,d]cyclohepten-5-ylidene)-propyl]-phenyl}-methanesulfonamide (218 mg, 0.49 mmol) is combined with ethanol (5 mL) in a scintillation vial. The sample is heated to approximately 75° C. with stirring. A 1 molar equivalence of HCl (1N) is added. After a few hours of elevated heating and stirring, the sample is allowed to cool to approximately 25° C. with stirring overnight. No precipitation occurs and the sample is evaporated to dryness under a nitrogen stream. To the resulting residue is added "wet" EtOAc (6 mL) which is prepared by washing the EtOAc with water in a separatory funnel to give approximately 3% water/EtOAc. The resulting suspension is stirred and heated at approximately 65° C. for several hours. The sample is allowed to cool to approximately 25° C. with stirring overnight. The solid is isolated from the suspension by vacuum filtration and allowed to air dry. The melting point characteristics of the material are determined by differential thermal analysis (DTA). Decomposition=180° C.

Example 5

(E)-N-{3-[1-(8-Chloro-11H-10-oxa-1-aza-dibenzo[a,d]cyclohepten-5-ylidene)-propyl]-phenyl}-methanesulfonamide (crystalline) (Form I)

Initial Analyses:
A sample of (E)-N-{3-[1-(8-chloro-11H-10-oxa-1-azadibenzo[a,d]cyclohepten-5-ylidene)-propyl]-phenyl}-methanesulfonamide, prepared essentially as described in Example I(a) is analyzed by differential scanning calorimetry and X-ray powder diffraction (before and after light grinding). DSC: onset 189.79° C.; peak 109.91° C.
Recrystallization:
Samples of the methansulfonamide from Example I(a) (about 50 mg) are dissolved in isopropyl alcohol, isopropyl acetate, acetonitrile, methanol, ethanol (absolute), ethanol (96%), and acetone by adding the solvents step by step under agitation at room temperature until complete dissolution. In cases where undissolved particles remain, the solution is heated to about 50° C. Each solution is then left in an open vial at room temperature under agitation until crystallization occurs (several hours to overnight). Evaporation is continued to allow sufficient crystal formation until about 0.5 ml of solution remains (about 0.2 ml for acetone solution). Once sufficient crystals have formed, the solutions are filtered and the resulting powders are dried on glass plates overnight under air at room temperature. Samples of the powders obtained from each of the recrystallizations are then analyzed by X-ray powder diffraction.
The X-ray patterns are obtained for the samples in the initial analyses (before and after grinding), as well as for the recrystallized samples and reveal a common crystal form (Form I) having characteristic peak positions (°2θ values) in common with the following obtained from the initial sample after light grinding:

| Peak # | °2θ | I/Io |
|---|---|---|
| 1 | 10.9 | 0.51 |
| 2 | 15.8 | 0.28 |
| 3 | 16.9 | 0.43 |
| 4 | 18.8 | 1.00 |
| 5 | 20.5 | 0.41 |
| 6 | 22.9 | 0.96 |
| 7 | 29.7 | 0.27 |
| 8 | 31.8 | 0.19 |

Example 6

(E)-N-{3-[1-(8-Chloro-11H-10-oxa-1-aza-dibenzo[a,d]cyclohepten-5-ylidene)-propyl]-phenyl}-methanesulfonamide (methanol recrystallization)

A 50 L three neck round bottom flask is equipped with a mechanical stirrer, reflux condenser, thermocouple and drying tube and placed in a heating mantle. 2263 g of solid material, prepared essentially as described in Example I(b), and MeOH (30 L) are charged to the flask. Stirring is initiated and the mixture heated to reflux with continued heating until all the solids are dissolved. Once a clear solution is obtained, charcoal (180 g) is carefully added to the flask. The mixture is filtered while hot and the filtrate charged to a 50 L three neck round bottom flask equipped with a mechanical stirrer, thermocouple and drying tub placed in a cooling tub. The resulting solution is cooled slowly at first, then to −10 to 0° C. and stirred at this temperature for a minimum of one hour. After this time the solids are collected by filtration and washed with cold MeOH (2×600 mL, −40° C.). The product is dried in a vacuum oven at 70° C. overnight to provide 1942 g.

Example 7

(E)-N-{3-[1-(8-Chloro-11H-10-oxa-1-aza-dibenzo[a,d]cyclohepten-5-ylidene)-propyl]-phenyl}-methanesulfonamide (micronized)

Samples of Compound (I) (prepared, for example, essentially as described in Example 6) are reduced in particle size (micronized) using a series 0101 Jet-O-Mizer (loop mill) (Fluid Energy Processing and Equipment Company) and compressed nitrogen milling gas (dew point>40° C.). Particle size distribution is measured on a Sympatec (HELOS Particle Size Analysis system) laser diffraction particle size analyzer and the $x_{50}$ and $x_{90}$ particle sizes are determined. $x_{50}$<5 μm; $x_{90}$<15 μm.

Example 8

(E)-N-{3-[1-(8-Chloro-11H-10-oxa-1-aza-dibenzo[a,d]cyclohepten-5-ylidene)-propyl]-phenyl}-methanesulfonamide (crystalline) (Form II)

Samples of unmicronized Compound (I), prepared, for example essentially as described in Example 6, and micronized Compound (I), prepared, for example essentially as described in Example 7, are subjected to X-ray powder diffraction analysis using a Bruker D8 Advance diffractometer, with samples being scanned between 2° and 45° in °2θ, with a step size of 0.02° in 2θ and a scan rate of 5 second/step, with 0.6 mm divergence slit, 0.6 mm anti-scatter slit, 0.1 mm receiving slit and a 0.6 mm detector slit. The X-ray patterns for the unmicronized and micronized samples reveal a common crystal form (Form II) having characteristic peak positions at the following °2θ values:

| Peak # | °2θ |
|---|---|
| 1 | 4.5 |
| 2 | 9.0 |
| 3 | 11.5 |
| 4 | 14.7 |
| 5 | 16.4 |
| 6 | 17.2 |
| 7 | 24.5 |
| 8 | 27.7 | probe sonicated formulation is determined using a Horiba LA-920 particle size analyzer: average particle size: 3.8 μm; d90 particle size: 6.5 μm.

The probe sonicated formulation is then homogenized to provide a nanosuspension using a Microfluidics M-110S Microfluidizer equipped with a JR30, 75 micron, interaction chamber and a cooling coil. The cooling coil is maintained in a water bath kept at a temperature of 20-30° C. except for brief excursions as low as 14° C. and as high as 39° C. The pressure gauge is set at 100 psi (about 6.89 bar) which applies a pressure of 23,000 psi on the formulation. The formulation is contained in a 1 L hopper and is drawn into the Microfluidizer from the bottom of the hopper and returned to the top of the liquid in the hopper through the product drain and a length of silicone tubing. The formulation is also stirred in the hopper with standard propeller mixer. The entire volume of the formulation is passed through the interaction chamber 81 times. The final particle size of Compound I in the nanosuspension formulation is determined using a Horiba LA-920 particle size analyzer: average particle size: 0.430 μm; d90 particle size: 0.594 μm.

```
                        SEQUENCE LISTING

<160> NUMBER OF SEQ ID NOS: 2

<210> SEQ ID NO 1
<211> LENGTH: 15
<212> TYPE: DNA
<213> ORGANISM: Artificial
<220> FEATURE:
<223> OTHER INFORMATION: Synthetic Construct

<400> SEQUENCE: 1
ggttcttgga gtact                                                   15

<210> SEQ ID NO 2
<211> LENGTH: 15
<212> TYPE: DNA
<213> ORGANISM: Artificial
<220> FEATURE:
<223> OTHER INFORMATION: Synthetic Construct

<400> SEQUENCE: 2
tgtacaggat gttct                                                   15
```

Example 9

(E)-N-{3-[1-(8-Chloro-11H-10-oxa-1-aza-dibenzo[a,d]cyclohepten-5-ylidene)-propyl]-phenyl}-methanesulfonamide in nanosuspension About 579 mg of Compound I having an initial d90 particle size=32 μm (initial particle size determined using a Beckman Coulter LS13 320 Laser Diffraction Particle Size Analyzer) is suspended in 174 mL of a vehicle comprising 1% sodium carboxymethyl cellulose, 0.25% polysorbate 80, and 0.05% Antifoam 1510 in a 250 mL Pyrex No. 1395 media bottle. The formulation is then sonicated with a Branson Sonifer 250 for 46 min using a 0.5 inch probe at a power output that is about 86% of maximum. The particle size of Compound I in the

What is claimed is:

1. A compound which is (E)-N-{3-[1-(8-Chloro-11H-10-oxa-1-aza-dibenzo[a,d]cyclohepten-5-ylidene)-propyl]-phenyl}-methanesulfonamide, or a pharmaceutically acceptable salt thereof.

2. The compound according to claim 1 which is (E)-N-{3-[1-(8-Chloro-11H-10-oxa-1-aza-dibenzo[a,d]cyclohepten-5-ylidene)-propyl]-phenyl}-methanesulfonamide.

3. A salt according to claim 1 which is (E)-N-{3-[1-(8-Chloro-11H-10-oxa-1-aza-dibenzo[a,d]cyclohepten-5-ylidene)-propyl]-phenyl}methanesulfonamide.HBr,(E)-N-{3-[1-(8-Chloro-11H-10-oxa-1-aza-dibenzo[a,d]cyclohepten-5-ylidene)-propyl]-phenyl}-methanesulfonamide.HCl, or (E)-N-{3-[1-(8-Chloro-11H-10-oxa-1-aza-dibenzo[a,d]cyclohepten-5-ylidene)-propyl]-phenyl}-methanesulfonamide.$H_2SO_4$ (2:1).

4. A method of treating rheumatoid arthritis comprising administering to a patient in need thereof an effective amount of a compound or salt according to claim 1.

5. The method according to claim 4 comprising administering to a patient in need thereof an effective amount of a compound which is (E)-N-{3-[1-(8-Chloro-11H-10-oxa-1-aza-dibenzo[a,d]cyclohepten-5-ylidene)-propyl]-phenyl}-methanesulfonamide.

6. A pharmaceutical composition comprising a compound or salt according to claim 1 in combination with one or more pharmaceutically acceptable carriers, excipients, or diluents.

7. A pharmaceutical composition according to claim 6 comprising a compound which is (E)-N-{3-[1-(8-Chloro-11H-10-oxa-1-aza-dibenzo [a,d]cyclohepten-5-ylidene)-propyl]-phenyl}-methanesulfonamide in combination with one or more pharmaceutically acceptable carriers, excipients, or diluents.

\* \* \* \* \*

UNITED STATES PATENT AND TRADEMARK OFFICE
CERTIFICATE OF CORRECTION

PATENT NO.          : 8,101,760 B2
APPLICATION NO.     : 12/305295
DATED               : January 24, 2012
INVENTOR(S)         : Matthew William Carson et al.

Page 1 of 1

It is certified that error appears in the above-identified patent and that said Letters Patent is hereby corrected as shown below:

On the cover page of the patent, under the section titled "Prior Publication Data," please add an additional section titled --Related U.S. Application Data--. Under the new heading titled "Related U.S. Application Data," please add the following sentence --Provisional application No. 60/831,166, filed on July 14, 2006.--

On the cover page of the patent, Column 2, under the heading "Other Publications," line 15, please delete the word "Dibenzoxapine" and insert --Dibenzoxazepine--, therefor.

On the cover page of the patent, Column 2, under the heading "Other Publications," line 18, please delete the word "Dibenzoxapine" and insert --Dibenzoxazepine--, therefor.

In Column 42, line 62, in Claim 3, delete "}methanesulfonamide" and insert --}-methanesulfonamide--, therefor.

Signed and Sealed this
Thirteenth Day of March, 2012

David J. Kappos
*Director of the United States Patent and Trademark Office*